US008968265B2

(12) United States Patent
Kline et al.

(10) Patent No.: US 8,968,265 B2
(45) Date of Patent: Mar. 3, 2015

(54) ABSORBENT ARTICLE FASTENING DEVICE HAVING STIFFNESS CHANGING CHARACTERISTICS

(75) Inventors: Mark James Kline, Okeana, OH (US); Jeromy Thomas Raycheck, Lebanon, OH (US); Arman Ashraf, Hamilton, OH (US); Urmish Popatal Dalal, Milford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1389 days.

(21) Appl. No.: 11/240,727

(22) Filed: Sep. 30, 2005

(65) Prior Publication Data

US 2007/0078426 A1   Apr. 5, 2007

(51) Int. Cl.
*A61F 13/15*   (2006.01)
*A61F 13/56*   (2006.01)
*A61F 13/62*   (2006.01)

(52) U.S. Cl.
CPC ............. *A61F 13/5622* (2013.01); *A61F 13/62* (2013.01)
USPC ............................ 604/390; 604/386; 604/387

(58) Field of Classification Search
USPC ..................... 604/385.03, 386–391
See application file for complete search history.

(56) References Cited

U.S. PATENT DOCUMENTS

| | | | |
|---|---|---|---|
| 3,860,003 A | 1/1975 | Buell | |
| 3,929,135 A | 12/1975 | Thompson | |
| 4,051,853 A | 10/1977 | Egan | |
| 4,324,246 A | 4/1982 | Mullane et al. | |
| 4,342,314 A | 8/1982 | Radel et al. | |
| 4,463,045 A | 7/1984 | Ahr et al. | |
| 4,515,595 A | 5/1985 | Kievit et al. | |
| 4,643,729 A | 2/1987 | Laplanche | |
| 4,695,278 A | 9/1987 | Lawson | |
| 4,834,735 A | 5/1989 | Alemany et al. | |
| 4,892,536 A | 1/1990 | DesMarais et al. | |
| 4,908,247 A | 3/1990 | Baird et al. | |
| 4,909,803 A | 3/1990 | Aziz et al. | |
| 4,940,464 A | 7/1990 | Van Gompel et al. | |
| 4,990,147 A | 2/1991 | Freeland | |

(Continued)

FOREIGN PATENT DOCUMENTS

| | | | | |
|---|---|---|---|---|
| GB | 2 303 046 B | * | 9/1999 | ............... A61F 13/15 |
| WO | WO95/16746 | | 6/1995 | |

(Continued)

OTHER PUBLICATIONS

PCT International Search Report, May 2, 2007, 4 pages.

(Continued)

*Primary Examiner* — Michele M Kidwell
(74) *Attorney, Agent, or Firm* — Christian M. Best; Charles R. Ware

(57) ABSTRACT

The present invention relates to a disposable absorbent article comprising a chassis defining a front waist region, a back waist region, and a crotch region disposed between the front waist region and back waist region. The article includes a fastening system that includes one or more fastening devices, each having at least one tab member configured to releasably connect to a slot member when, for instance, fastening the article to the body of the wearer. A variable stiffness member is associated with at least a portion of the fastening device that, in response to a predetermined external stimulus, reduces its stiffness to correspondingly reduce the stiffness of the fastening device.

23 Claims, 15 Drawing Sheets

(56) References Cited

U.S. PATENT DOCUMENTS

| | | |
|---|---|---|
| 5,006,394 A | 4/1991 | Baird |
| 5,037,416 A | 8/1991 | Allen et al. |
| 5,092,861 A | 3/1992 | Nomura et al. |
| 5,092,862 A | 3/1992 | Muckenfuhs et al. |
| 5,151,092 A | 9/1992 | Buell et al. |
| 5,221,274 A | 6/1993 | Buell et al. |
| 5,221,276 A * | 6/1993 | Battrell ............ 604/389 |
| 5,246,433 A | 9/1993 | Hasse et al. |
| 5,269,775 A | 12/1993 | Freeland et al. |
| 5,518,801 A | 5/1996 | Chappell et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,588 A | 7/1997 | Roe et al. |
| 5,807,371 A | 9/1998 | Toyoda et al. |
| 5,865,823 A | 2/1999 | Curro |
| 5,897,545 A | 4/1999 | Kline et al. |
| 5,957,908 A | 9/1999 | Kline et al. |
| 6,004,306 A | 12/1999 | Robles et al. |
| 6,120,487 A | 9/2000 | Ashton |
| 6,120,489 A | 9/2000 | Johnson et al. |
| 6,432,098 B1 | 8/2002 | Kline et al. |
| 6,791,004 B2 | 9/2004 | Sprengard-Eichel et al. |
| 2003/0088220 A1 | 5/2003 | Molander et al. |
| 2003/0233082 A1 | 12/2003 | Kline et al. |
| 2004/0021130 A1 | 2/2004 | Smith et al. |
| 2004/0055123 A1 | 3/2004 | Jackson et al. |

FOREIGN PATENT DOCUMENTS

| | | | |
|---|---|---|---|
| WO | 98/55061 | * 12/1998 | ............ A61F 13/15 |
| WO | WO 98/55061 | 12/1998 | |

OTHER PUBLICATIONS

Written Opinion, PCT/IB2006/053552, date of mailing Feb. 5, 2007.

* cited by examiner

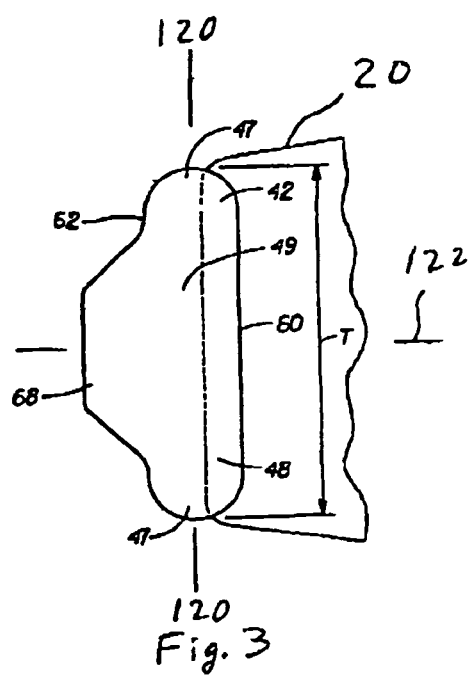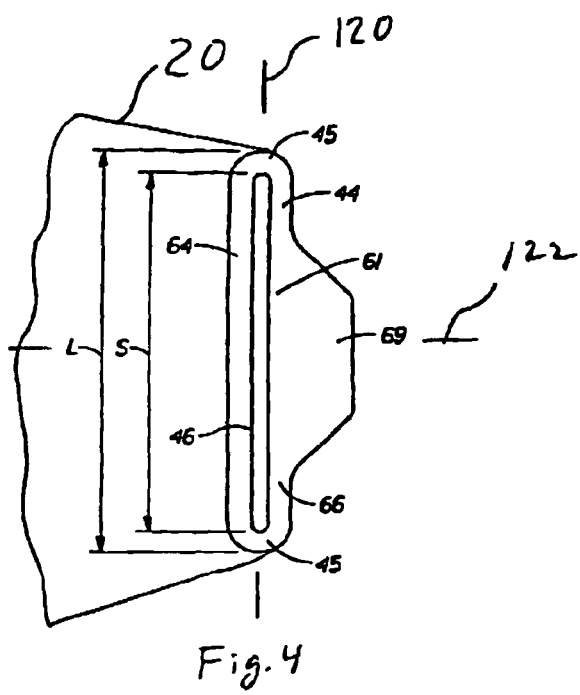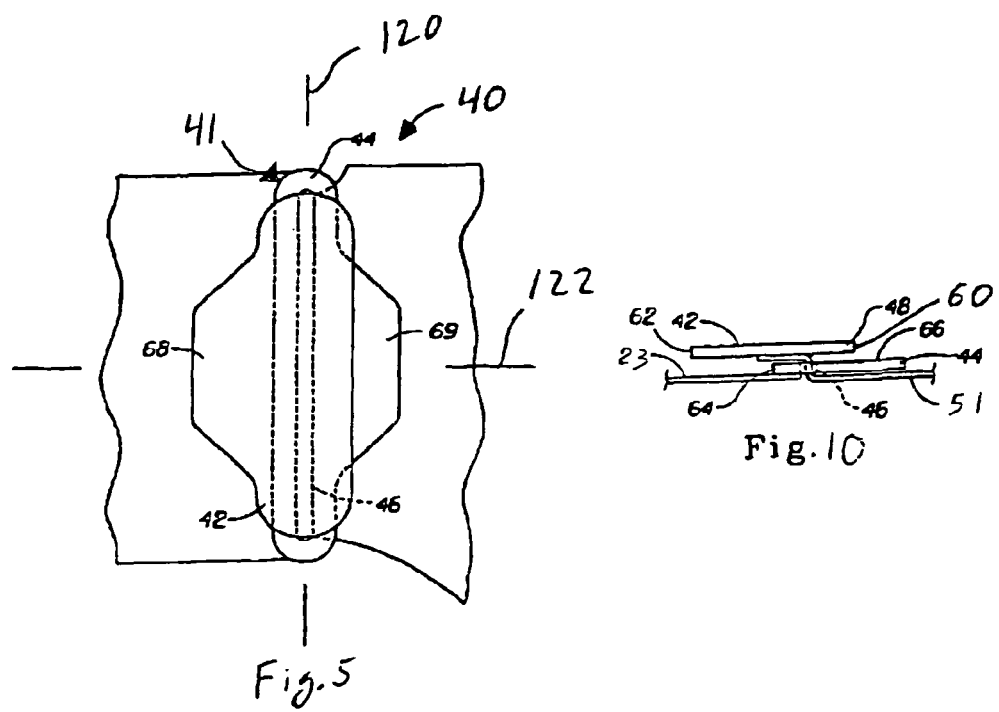

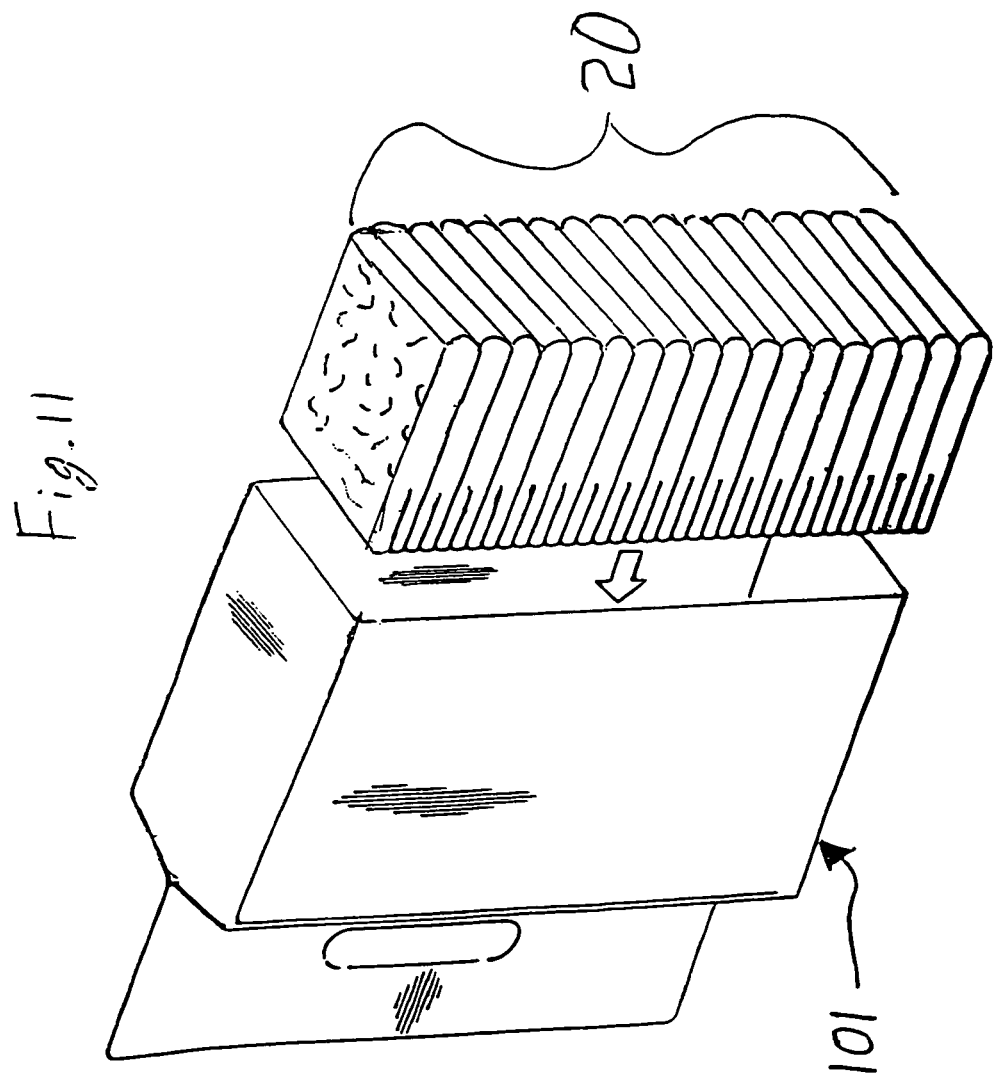

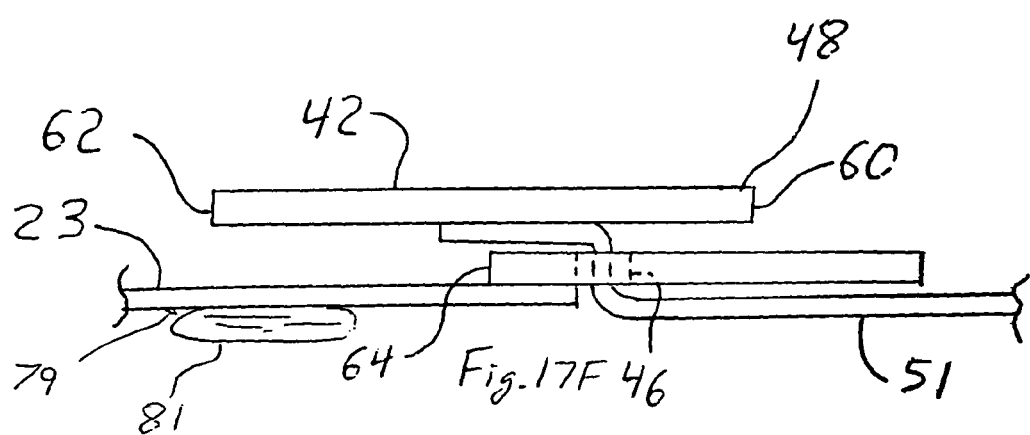
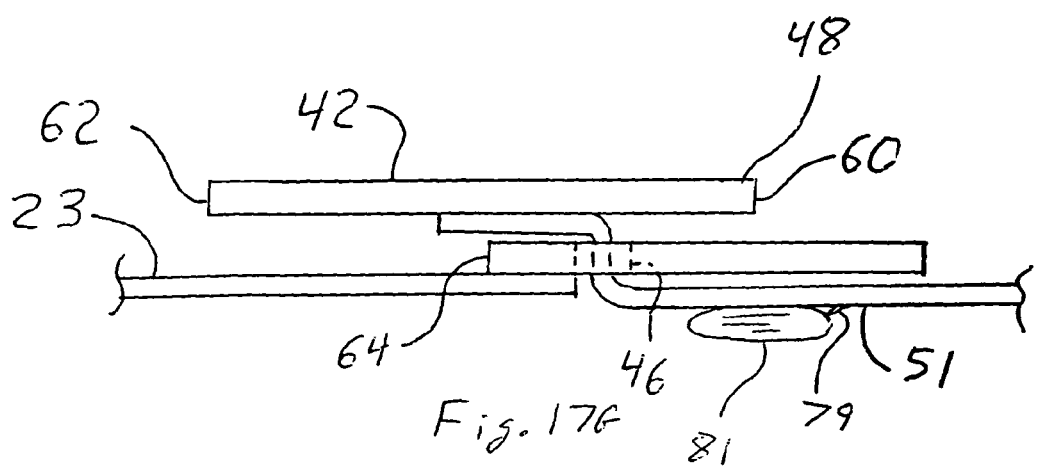

ABSORBENT ARTICLE FASTENING DEVICE HAVING STIFFNESS CHANGING CHARACTERISTICS

CROSS-REFERENCE TO RELATED APPLICATIONS

-

FIELD OF INVENTION

This invention relates to fastening systems for fastening absorbent articles onto a wearer, and in particular relates to fastening systems having stiffness characteristics that change during use.

BACKGROUND OF THE INVENTION

It has long been known that absorbent articles such as conventional taped diapers, pull-on diapers, training pants, sanitary napkins, pantiliners, incontinence briefs, and the like, offer the benefit of receiving and containing urine and/or other bodily exudates. To effectively contain exudates, the articles should provide a snug fit around the waist and legs of a wearer. Absorbent articles are known to have a chassis comprising a topsheet, a backsheet, an absorbent core, and barrier and/or gasketing cuffs. Pull-on diapers typically include side panels which attach the front waist region to the back waist region at a side panel interface, thereby forming a waist opening and a pair of leg openings.

It is well known that the side panel interface can include a refastenable fastening system that releasably connects the front and back waist regions, thereby advantageously permitting versatile changing (e.g., the wearer can be changed in a standing or lying position). Among known releasable fastening systems, hook-and-loop (e.g., Velcro®) or adhesive tapes require alignment of an engaging surface with a landing surface, thus often resulting in misapplication and/or poor alignment of the elements being connected. Furthermore, hook-and-loop fasteners can become ineffective due to compression and contamination or can harm surrounding materials. With an adhesive system, improperly fastening the device can render the entire product unusable. For instance, in diaper applications, attempting to reposition a tape tab which has been improperly fastened can result in tearing the outer diaper cover. Furthermore, adhesive-based systems are prone to contamination-induced performance problems. Other systems, such as buttons, snaps, hooks and eyes, and ties are limited in that they only connect at discrete points.

Accordingly, a tab-and-slot fastening system was developed as described in U.S. Pat. No. 6,432,098 which issued to Mark J. Kline, et al. on Aug. 13, 2002. The tab and slot fastening system typically includes a tab member disposed at a first location on the diaper, and a slot member disposed at a second location on the diaper opposed to the first location. The slot member defines a slot that receives the tab member in order to connect the fastening system. Specifically, the tab member is passed through the slot and is subsequently pivoted such that a portion of the tab member engages an edge of the slot to prevent the tab member from passing back through the slot member.

Tab-and-slot fastening systems of this type have been widely accepted for their ability to provide for a user-friendly refastenable connection along a length or span rather than at discrete points on the diaper. Furthermore, tab-and-slot fastening devices conform to different shapes and thus accommodate the wearer in seated, standing, and lying positions and maintain a reliable connection while the wearer is active. Moreover, tab-and-slot fastening devices can be connected and disconnected in many different configurations, thus allowing, for instance, an infant's diaper to be changed regardless of whether the infant is lying on a changing table or standing.

However, if the tab-and-slot fastening system members are not sufficiently rigid prior to connecting the fastening system, the user may have difficulty ensuring that the tab member is unable to pass back through the slot member. In particular, if either fastener element deforms significantly during the fastening process, the two members will form shapes that do not readily mate together. On the other hand, if the fastening system substantially maintains its rigidity after the fastening system connection, the tab and slot members can press into the abdomen or other bodily area of the wearer and cause discomfort and/or skin marking and/or irritation.

What is therefore needed is a fastening system having a stiffness that changes from a first level suitable for reliable fastening to a reduced level that eliminates or reduces instances of wearer discomfort and/or skin marking and/or irritation during use.

BRIEF DESCRIPTION OF THE INVENTION

The present invention is directed to an improved fastening system suitable for use with disposable absorbent articles. The fastening system can include one or more fastening devices that can each include connecting members to secure the article on the body of the wearer. At least one of the fastening devices incorporates a stiffness reducing characteristic that limits the ability of at least one of the fastening device members to press into the body of the wearer and cause discomfort and/or skin marking and/or irritation.

In accordance with one aspect of the present invention, an absorbent article is provided having a front waist region, a back waist region opposed to the front waist region and a crotch region located between the front waist region and the back waist region, a pair of longitudinal edges and a pair of end edges. The absorbent article includes a topsheet, a backsheet attached to the topsheet, and an absorbent core positioned between the topsheet and the backsheet. The absorbent article further includes a fastening system, which includes at least one fastening device configured to connect a first article location to a second article location. The fastening device includes a variable stiffness member having an original stiffness. The variable stiffness member undergoes a stiffness reduction in response to a predetermined stimulus to achieve a reduced stiffness that is less than the original stiffness.

In accordance with another aspect of the invention, a fastening device is provided for fastening a first member to a second member. The fastening device includes 1) a first fastener element extending from the first member; and 2) a second fastener element extending from the second member at a location opposed to the slot member, the second fastener element being configured to engage the first fastener element. The fastening device further includes a variable stiffness member having an original stiffness, wherein the variable stiffness member undergoes a stiffness reduction in response to a predetermined stimulus to achieve a reduced stiffness that is less than the original stiffness.

In accordance with yet another aspect of the invention, a method is provided for releasable fastening an absorbent article onto the body of a wearer. The article can be of the type having a front waist region, a back waist region opposed to the front waist region, and a crotch region located between the front waist region and the back waist region. The article includes a fastening device including a tab member configured to releasably connect to a slot member to fasten the article onto the body of the wearer. The fastening device includes a variable stiffness member having a stiffness that becomes reduced in response to a predetermined stimulus. The method includes the steps of (A) connecting the tab and slot members; (B) applying the predetermined stimulus to the variable stiffness member; and (C) reducing a stiffness of the fastening device.

BRIEF DESCRIPTION OF THE DRAWINGS

Reference is hereby made to the following figures in which like reference numerals correspond to like elements throughout, and in which:

FIG. 3 is a plan view of a tab member of the fastening device;

FIG. 4 is a plan view of a slot member of the fastening device;

FIG. 5 is a plan view of the fastening device in its fastened configuration;

FIG. 10 is an end view of the embodiment of the fastening device shown in FIG. 5;

FIG. 11 is a schematic side elevation view of a plurality of pre-fastened absorbent articles being packaged;

FIG. 17F is a schematic end view of a fastening device incorporating the deflatable bladder in accordance with an alternative embodiment;

FIG. 17G is a schematic end view of a fastening device incorporating the deflatable bladder in accordance with an alternative embodiment;

DEFINITIONS

Figure 1:
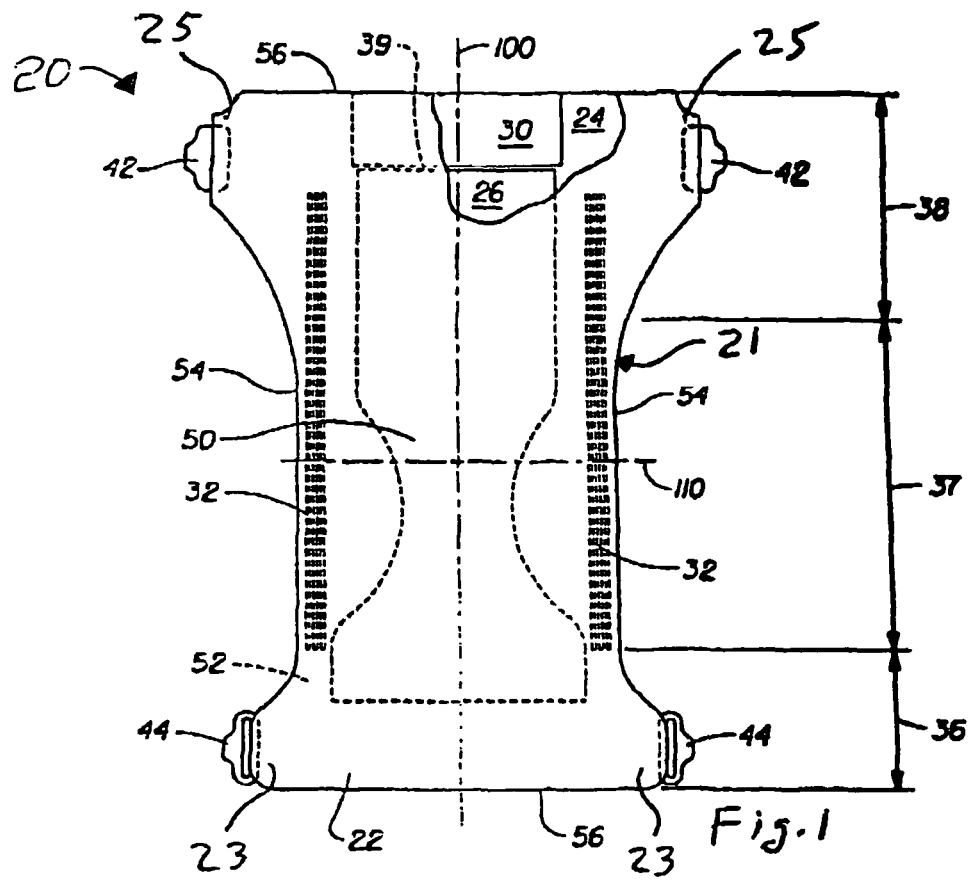
FIG. 1 is a plan view of an exemplary absorbent article having a fastening device, wherein the absorbent article is positioned in its flat out uncontracted state (i.e., without elastic induced contraction), with the body-facing surface facing the viewer, having portions cut-away.

As used herein, the following terms shall have the meaning specified thereafter:

The term "disposable," as used herein in reference to absorbent articles, means that the absorbent articles are generally not intended to be laundered or otherwise restored or reused as absorbent articles (i.e., they are intended to be discarded after a single use and, optionally, to be recycled, composted or otherwise discarded in an environmentally compatible manner).

The term "absorbent article" as used herein refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

The term "diaper" as used herein refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

The term "mechanical bond" as used herein is an attachment between two or more elements, components, regions, or webs and can comprise heat bonds, pressure bonds, ultrasonic bonds, dynamic mechanical bonds, or any other suitable non-adhesive attachment means or combinations of these attachment means as are known in the art.

The terms "proximal" and "distal" as used herein refer respectively to the location of an element relatively near to or far from the center of a structure (e.g., the proximal edge of a longitudinally extending element is located nearer to the longitudinal axis than the distal edge of the same element is located relative to the same longitudinal axis).

The terms "body-facing" and "garment-facing" as used herein refer respectively to the relative location of an element or a surface of an element or group of elements. "Body-facing" implies the element or surface is nearer to the wearer during wear. "Garment-facing" implies the element or surface is more remote from the wearer during wear (i.e., element or surface is nearer to the wearer's garments that can be worn over the disposable absorbent article).

The term "longitudinal" as used herein refers to a direction running substantially perpendicular from a waist edge to an opposing waist edge of the article and generally parallel to the maximum linear dimension of the article. Directions within 45 degrees of the longitudinal direction are considered to be "longitudinal."

The term "lateral" as used herein refers to a direction running from a longitudinal edge to an opposing longitudinal edge of the article and generally at a right angle to the longitudinal direction. Directions within 45 degrees of the lateral direction are considered to be "lateral."

The term "z-direction" as used herein refers to a direction running orthogonal to both the lateral and longitudinal directions. Directions within 45 degrees of the z-direction direction are considered to be in the "z-direction."

The term "disposed" as used herein refers to an element being attached and positioned in a particular place or position in a unitary structure with other elements.

The term "attached" as used herein refers to configurations whereby an element is directly secured to another element by affixing the element directly to the other element and to configurations whereby an element is indirectly secured to another element by affixing the element to intermediate member(s) which in turn are affixed to the other element.

The terms "water-permeable" and "water-impermeable" as used herein refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure. A layer or a layered structure that is water-impermeable according to this definition can be permeable to water vapor, i.e., can be "vapor-permeable." As is well known in the art, a common method for measuring the permeability to water, urine, or synthetic urine of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables and Nonwovens Association).

The terms "extendable" and "extensible" as used herein mean that the width or length of the component in the relaxed position can be extended or increased.

The terms "elastic," "elastomer," and "elastomeric" as used herein refer to a material which generally is able to extend to a strain of at least 50% without breaking or rupturing, and is able to recover substantially to its original dimensions after the deforming force has been removed.

The terms "outboard" and "inboard" as used herein refer respectively to the location of an element disposed relatively far from or near to an axis of the diaper with respect to a second element. For example, if element A is outboard of element B, then element A is farther from the longitudinal axis than is element B.

The terms "pant", "training pant", "closed diaper", "prefastened diaper", "pull-on garment", and "pull-on diaper", as used herein, refer to disposable garments having a waist opening and leg openings designed for infant or adult wearers. A pant can be configured such that the pant has a closed waist and leg openings prior to being donned on the wearer, or the pant can be configured such that the waist is closed and the leg openings formed while on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, back waist fastened). Examples of suitable pants are disclosed in U.S. Pat. No. 5,246,433; U.S. Pat. No. 5,569,234; U.S. Pat. No. 6,120,487; U.S. Pat. No. 6,120,489; U.S. Pat. No. 4,940,464; U.S. Pat. No. 5,092,861; U.S. Pat. No. 5,897,545; U.S. Pat. No. 5,957,908; and U.S. Patent Publication No. 2003/0233082 A1.

The term "variable stiffness member" refers to any structure, either integral with an absorbent article or component thereof, or added to an absorbent article or component thereof, that is configured to undergo a reduction in stiffness in response to a predetermined stimulus.

The term "integral variable stiffness member" refers to any material, layer, or structure that forms at least a portion of a fastening member and that is configured to undergo a stiffness reduction in response to an external stimulus.

The term "external variable stiffness member" refers to any material, layer, or structure that is attached to a fastener element or operatively associated with a fastener element such that a stiffness reduction of the external variable stiffness member in response to an external stimulus reduces the stiffness of the fastening device.

The term "external stimulus" as used herein refers to any stimulus, whether applied directly or indirectly, whose source is external to the absorbent article, that affects stiffness.

The term "internal stimulus" as used herein refers to any stimulus, whether applied directly or indirectly, whose source is integral with absorbent article, that affects stiffness.

The terms "tab member" and "slot member" refer to a "tab element" and "slot element," respectively, that are attached to the absorbent article or formed integrally with the absorbent article.

The term "associated with" in the context of a variable stiffness member refers to the member being directly attached, indirectly attached, or integral with a component such that the stiffness of the variable stiffness member affects the stiffness of the component to which the variable stiffness member is associated.

DETAILED DESCRIPTION OF THE INVENTION

Figure 2:
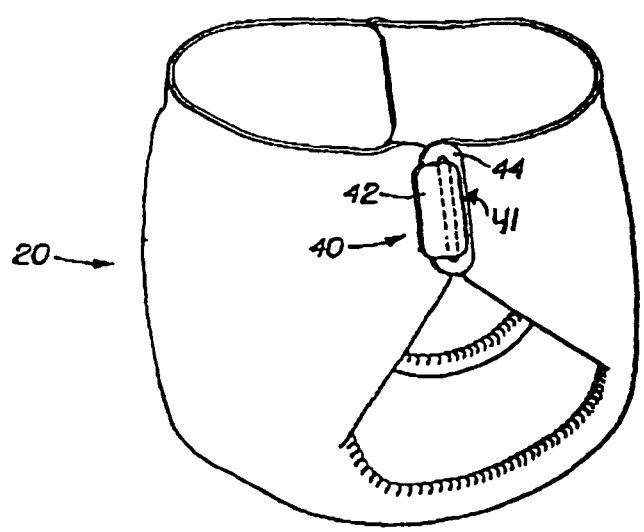
FIG. 2 is a perspective view of the absorbent article with its fastening device in a fastened configuration.

Referring to FIGS. 1 and 2, an absorbent article 20, such as a sanitary napkin, a bib, a training pant, an incontinence pad, a diaper, or other bodily wrap, extends along a longitudinal axis or centerline 100 and a lateral axis or centerline 110. As illustrated, the absorbent article 20 is a pull-on diaper (i.e., pant) that defines an outer surface 52 and an inner surface 50 facing opposite the outer surface 52. The inner surface 50 generally includes that portion of the diaper 20 which is positioned adjacent the wearer's body during use, while the outer surface 52 generally comprises that portion of the diaper 20 which is positioned away from the wearer's body.

The diaper includes a chassis 21 having a first, or front, waist region 36, a second, or rear, waist region 38 opposed to the front waist region 36, and a crotch region 37 located between the front waist region 36 and the back waist region 38. The waist regions 36 and 38 generally comprise those portions of the diaper 20 which, when worn, encircle the waist of the wearer. The waist regions 36 and 38 can include elastic elements such that they gather about the waist of the wearer to provide improved fit and containment. The crotch region 37 is that portion of the diaper 20 which, when the diaper 20 is worn, is generally positioned between the legs of the wearer. The outer periphery of the chassis 21 is defined by lateral end edges 56 that can be oriented generally parallel to the lateral axis 110, and by longitudinal edges 54 that can be oriented generally parallel to the longitudinal axis 100 or, for better fit, can be curved or angled to produce an "hourglass" shape diaper when viewed in a plan view. Longitudinal axis 100 bisects the end edge 56 while the lateral axis 110 bisects the longitudinal edge 54.

The chassis 21 can comprises a liquid pervious topsheet 22, a liquid impervious backsheet 24, and an absorbent core 26 positioned between the topsheet 22 and the backsheet 24. The absorbent core 26 can have a body-facing surface and a garment facing-surface. The topsheet 22 can be disposed adjacent the body-facing surface of the absorbent core 26, while the backsheet 24 can be disposed adjacent the garment-facing surface of the absorbent core 26. It should be appreciated that the topsheet 22 can be attached to the core 26 and/or the backsheet 24 and that the backsheet 24 can be attached to the core 26 and/or the topsheet 22. It should be recognized that other structures, elements, or substrates can be positioned between the core 26 and the topsheet 22 and/or backsheet 24. In certain embodiments, the chassis 21 comprises the main structure of the diaper 20 with other features added to form the composite diaper structure. While the topsheet 22, the backsheet 24, and the absorbent core 26 can be assembled in a variety of well-known configurations, certain diaper configurations are described generally in U.S. Pat. Nos. 3,860,003; 5,151,092; 5,221,274; 5,554,145; 5,569,234; 5,580,411; and 6,004,306. Topsheet 22, backsheet 24, and absorbent core 26 are discussed in more detail below.

The diaper 20 can include front ears 23 and back ears 25, which can be unitary elements of the diaper 20 (i.e., they are not separately manipulative elements secured to the diaper 20, but rather are formed from and are extensions of one or more of the various layers of the diaper). In certain embodiments, the front and/or back ears 23, 25 can be integral with the chassis 21 as shown in FIG. 1, or be discrete elements that are attached to the chassis 21. The front ears 23 and back ears 25 can be extensible, inextensible, elastic, or inelastic, and can be formed from nonwoven webs, woven webs, knitted fabrics, polymeric and elastomeric films, apertured films, sponges, foams, scrims, and combinations and laminates thereof. In certain embodiments the front ears 23 and back ears 25 can be formed of a nonwoven/elastomeric film laminate or a nonwoven/elastomeric film/nonwoven laminate. A suitable elastic ear 23, 25 can be a laminate comprising an elastomeric film (such as is available from Tredegar Corp, Richmond, Va., as supplier code X25007) disposed between two nonwoven layers (such as is available from BBA Fiberweb, Brentwood, Tenn. under supplier code FPN332).

Referring also to FIGS. 3-5, the diaper 20 further includes a fastening system 40 which attaches at least a portion of the front waist region 36 of the diaper 20 with at least a portion of the back waist region 38 to form leg and waist openings. The fastening system 40 can also work with a waist feature 30 (see FIG. 1) to maintain lateral tension in order to keep the diaper 20 in place about the wearer. The waist feature 30 is described in more detail below.

The fastening system 40 includes one or more (a pair as illustrated) fastening devices 41 which each comprises a first fastener element such as a tab member 42, and a second fastener element such as a slot member 44 extending along a longitudinal axis 120 and a lateral axis 122. A "tab member" is broadly defined herein as an attachment member, at least a portion of which is configured to be passed through a mating slot member 44 to provide a fastened connection, while a "slot member" is broadly defined herein as an attachment member configured to receive at least a portion of a tab member to provide a fastened connection. For the purposes of this description, the axes of the tab member 42 and slot member 44 are considered herein to be one and the same when the fastening device 41 is disconnected as they are when the fastening device 41 is connected.

Figure 6:
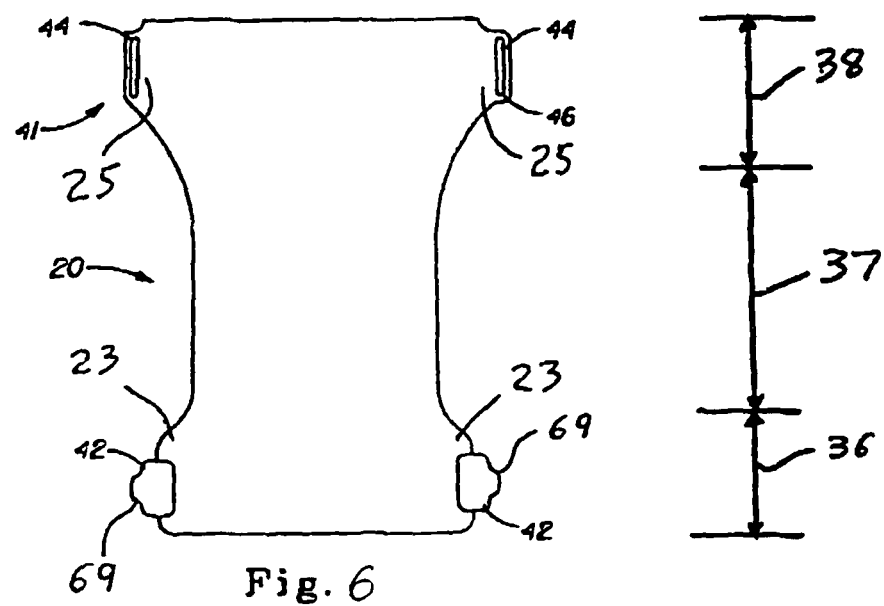
FIG. 6 is a plan view of an alternative absorbent article embodiment of the present invention in a flat out, uncontracted configuration.
Figure 7:
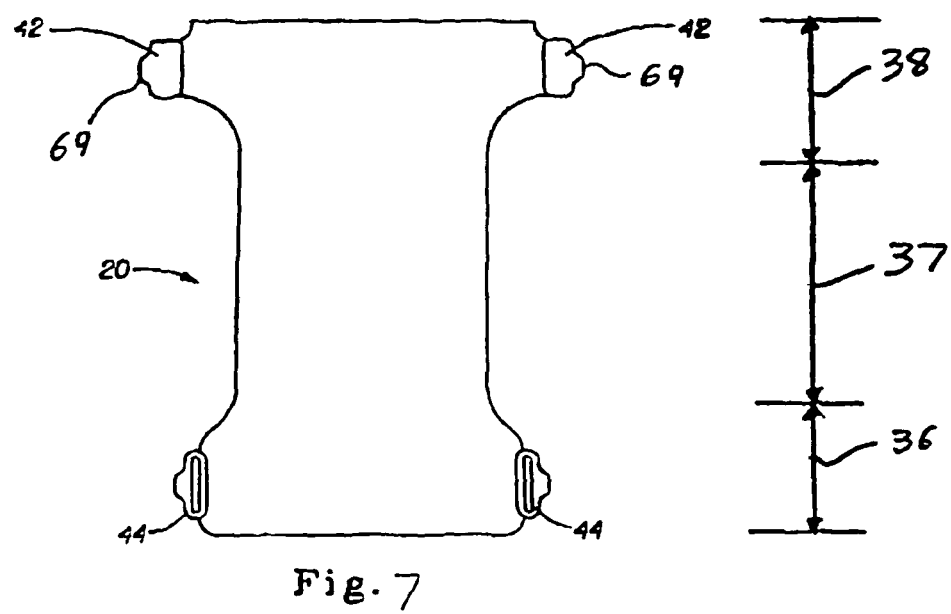
FIG. 7 is a plan view of another alternative absorbent article embodiment of the present invention in a flat out, uncontracted configuration.

Referring to FIGS. 6 and 7, the tab members 42 can be positioned at the front waist region 36 or the back waist region 38, for instance at the front ears 23 (FIG. 6) or back ears 25 (FIG. 7), or at any alternative desired location such that the tab member 42 can readily connect to the slot member 44. Alternatively, a tab member 42 can be laterally spaced from a slot member 44 at the front waist region 36, such that an opposing slot member 44 is laterally spaced from a tab member 42 at the back waist region 38. Numerous alternative configurations of the fastening system 40 that achieve a releasable connection between the front waist region 36 and back waist region 38 are contemplated by the present invention.

Referring now to FIG. 3 in particular, the tab member 42 can be an elongated member having a length T, a proximal edge 60, a distal edge 62, and a lip portion 48 generally adjacent at least a portion of the proximal edge 60. The tab member 42 has longitudinal ends 47 and a central region 49. The lip portion 48 is that portion of the tab member 42 which is not attached directly to the underlying structure of the article to which the tab member 42 is attached. As noted above, the lip portion 48 should lift away from the underlying structure of the article so that it can be positioned in an overlapping configuration with at least a portion of the slot member 44. Some embodiments of the tab member 42 can also include a grip portion 68 generally adjacent to and extending outwardly from the distal edge 62 of the tab member 42. The grip portion 68 helps the user grip the tab member 42 when fastening or releasing the fastening device 41 and extends from the distal edge 62 in the central region 49 of the tab member 42.

The tab member 42 can be of any size and/or shape and can be made from any suitable material such as plastics, films, foams, nonwoven webs, woven webs, paper, laminates, steel, fiber reinforced plastics and the like, or combinations thereof. The shape of the tab member 42 will often be dependent on the end use of the fastening device 41, but in any case should be aesthetically pleasing, easy to hold and maneuver, and capable of maintaining the device 41 in a fastened configuration throughout the intended period of use when subjected to expected forces and external conditions.

The tab member 42 can be attached to the article 20 at any location on the article. In a disposable absorbent article embodiment, the tab member 42 can be an extension of the material making up the back ear 25 (i.e., integral with the back ear 25). In such cases, it can be desirable to provide additional material or to process the material of the ears 25 so as to change some of its physical properties. For example, it may be desirable that the ear 25 be extensible while the tab member 42 is inextensible. Alternatively, the tab member 42 can be a separate element which is attached to the article 20 in any suitable manner known to one having ordinary skill in the art. Whether the tab member 42 is integral with the absorbent article 20 or attached to the article 20, the tab member can be said to "extend" from the article 20.

Figure 8:
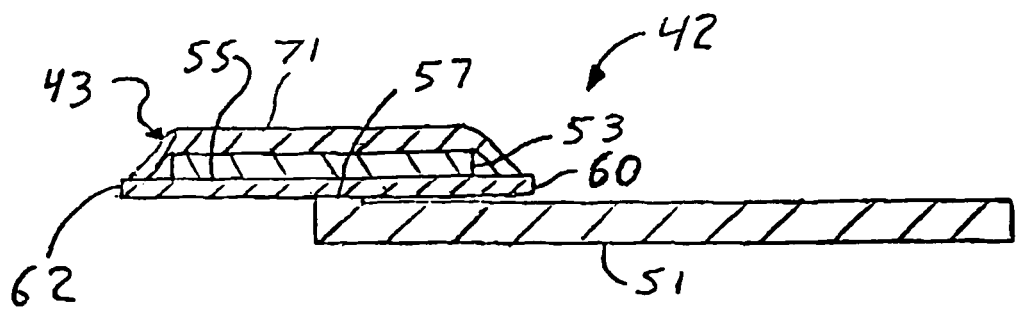
FIG. 8 is a sectional side elevation view of the tab member.

Referring now to FIG. 8, the tab member 42 can include at least one tab element 43 attached to a substrate carrier 51. The substrate carrier 51 can comprise at least a portion of, for instance, the front waist region 36 or back waist region 38 of the diaper 20. The tab element 43 can be attached to the substrate carrier 51 using any suitable adhesive or mechanical bond.

The tab element 43 can include, for instance, a core member 53 that has a stiffness greater than the remaining components that comprise the tab element 43 and, hence, provides the majority of the tab member stiffness. The core member 53 can, as illustrated, comprise a thermoplastic printed on a substrate layer 55 such as a nonwoven or any alternative material suitable for carrying a thermoplastic print. Methods of thermoplastic printing a tab element onto a substrate film are described in U.S. patent application Ser. No. 10/288,144 published May 8, 2003 as U.S. Patent Application Publication No. 2003/0088220 filed by John C. Molander, et al. Alternatively still, the core member 53 can be formed from any plastic or suitable material having a desired stiffness characteristic as described in U.S. Pat. No. 6,432,098 which issued to Mark J. Kline, et al. on Aug. 13, 2002.

The core member 53 can be sandwiched between at least a first substrate layer 55 and a second substrate layer 71 which can be coterminous about the periphery, or at least a portion of the periphery, of the core member 53. Specifically, the second substrate layer 71, which can comprise a nonwoven or suitable equivalent, extends beyond the core member 53 and is attached to that portion of the first substrate layer 55 that extends beyond the core member 53. At least one of the first substrate layer 55 and the second substrate layer 71 is attached to the substrate carrier 51.

In the illustrated embodiment, the middle portion of the tab element 43 is attached to the diaper 20 (e.g., topsheet 22 and/or backsheet 24) along a line of attachment 57, leaving the proximal and distal edges 60, 62 of tab member 42 directly unattached from the diaper layer. The line of attachment can extend at least about 25 percent, alternatively at least 50 percent, alternatively still at least 75 percent, and alternatively still substantially the entire the length of the tab element 43.

Referring now to FIG. 4, the slot member 44 is that portion of the fastening device 41 through which at least a portion of tab member 42 is passed in order to fasten the device 41. The slot member 44 extends from the absorbent article 20, and can thus be attached to the absorbent article 20 or formed integrally therewith. As illustrated, the slot member 44 is disposed at a front portion of article 20, for example at the front ears 23 (FIG. 7), though one having ordinary skill in the art will appreciate that the slot member 44 can be disposed at any suitable location on the article 20, for example at the back ears 25 (FIG. 6), or any alternative desired location such that the slot member 44 receives the tab member 42 to provide a desired connection. Further, the slot member 44 can be attached to the article at any suitable location. In a disposable absorbent article embodiment, the slot member 44 can be an extension of the material making up the ears 23, 25 or any other portion of the diaper 20.

The slot member 44 defines an inboard portion 64, an outboard portion 66, longitudinal ends 45 and a central region 61. A longitudinally extending slot 46 is disposed between the inboard portion 64 and the outboard portion 66 and spans between the longitudinal ends 45. The slot member 44 and the slot 46 have lengths L and S, respectively, with the length S of the slot 46 less than the length L of the slot member 44. However, the length S of the slot 46 should generally be greater than or equal to the length T of the tab member 42 such that the tab member 42 is easily passed through the slot 46 without undue bending or deformation of either component. The slot 46 can alternatively include a slit, which is defined as a slot having essentially no gap other than that left by a cutting process, a loop as defined in U.S. Pat. No. 6,432,098 which issued to Mark J. Kline, et al. on Aug. 13, 2002, or any alternative opening or void suitable to engage a fastener element in accordance with the principles of the present invention.

The slot member 44 can also include a grip portion 69 like that of the tab member 42. In one embodiment, the grip portion 69 extends laterally outwardly from the outboard portion 66 of the slot member 44. The grip portion 69 helps the user grip the slot member 44 when fastening or releasing the fastening device 41 and extends from the outboard portion 66 in the central region 61 of the slot member 44.

Figure 9:
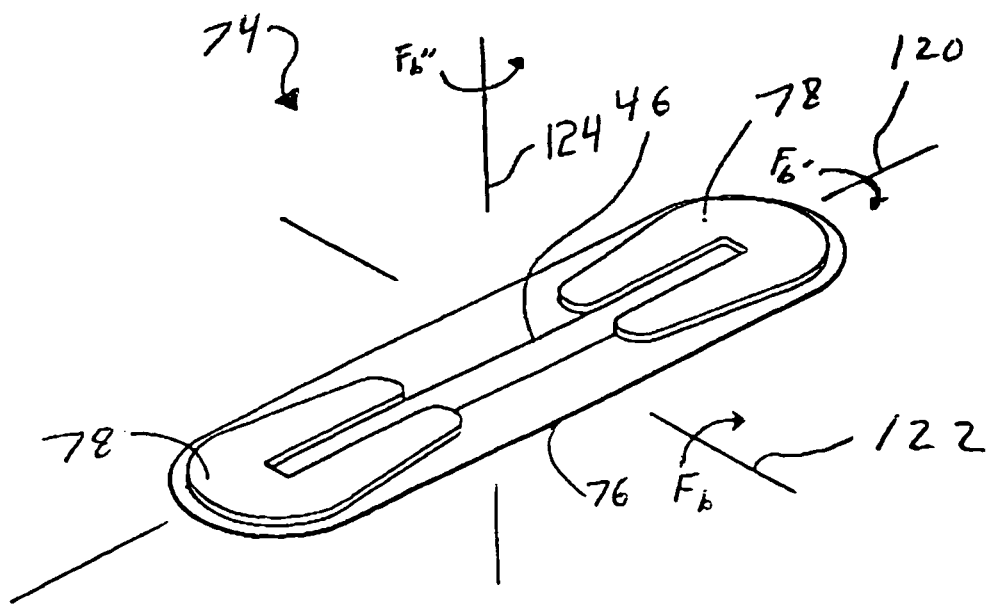
FIG. 9 is a perspective view of a slot element forming part of the slot member.

Referring to FIGS. 4 and 9, the slot member 44 constructed in accordance with certain aspects of the invention includes at least one slot element 74 that can either be attached to the article 20 or formed integrally with the article 20 to provide the slot member 44. It will thus be appreciated that the slot element 74 can be disposed between opposing substrate, such as nonwoven or suitable alternative material. The slot element 74 comprises a base member 76 (which can be integral with the article 20) that defines the central region 61 and opposing longitudinal ends 45.

As illustrated in FIG. 9, the slot member 44 is stronger at its longitudinal ends 45 than at its central region 61. Specifically, the longitudinal ends 45 are reinforced with an outer reinforcing member 78 disposed on the base member 76 at each opposing longitudinal end 45 to increase the strength of the slot member 44 locally at the longitudinal ends 45. The reinforcing member 78 can either be separate from and attached to the base member 76 or integrally formed with the base member 76, and can be formed from plastics, films, foams, nonwoven webs, woven webs, paper, laminates, steel, fiber reinforced plastics and the like, or combinations thereof as described above. As illustrated, the reinforcing member 78 is an inwardly facing substantially u-shaped member attached to the upper surface of the base member 76, though it should be appreciated that the reinforcing member 78 could assume any suitable shape and be disposed anywhere on the base member 76 that would benefit from a localized increase in strength and/or stiffness.

The slot 46 is formed through the base member 76, is elongated between longitudinal outer ends 45 along the direction of longitudinal axis 120, and extends between the reinforcing members 78. The slot 46 is substantially centrally disposed with respect to the lateral direction, and thus partially bisects the u-shaped reinforcing members 78.

The base member 76 can be formed from any suitable material having the ability to flex with the body and distribute localized pressures over a broader area to reduce local pressure that the fasteners exert on the user. Because the reinforcing members 78 support a majority of the load during use, they can be formed from a material having a high Young's modulus, a high yield, and a high modulus of resilience. In one embodiment, the base member 76 is formed from a low density polyethylene and the reinforcing member is formed from polypropylene, though one having ordinary skill in the art will recognize that the base member 76 could be formed from plastics, films, foams, nonwoven webs, woven webs, paper, laminates, steel, fiber reinforced plastics and the like, or combinations thereof or other material as described above.

Referring now to FIG. 10, during operation, the fastening device 41 is releasably fastened by passing distal edge 62 of the tab member 42 through the slot 46 of the slot member 44, followed by the proximal edge 60 of the tab member 42 such that the tab member 42 has been passed completely through the slot 46. Next, the lip portion 48 of the tab member 42 is rotated into a plane generally parallel with the plane of the slot member 44 such that at least a part of the lip portion 48 overlaps at least a part of the outboard portion 66 of the slot member 44, while the distal edge 62 of the tab member 42 overlaps the inboard portion 64 of the slot member 44. In this configuration, the lip portion 48 of the tab member 42 will prevent the tab member 42 from slipping back through the slot 46 and disengaging the fastening device 41. A portion of the tab member 42 or the material of the article to which the tab member 42 is joined will extend into the slot 46, as shown in FIG. 10. The material in the slot 46 will act to resist forces in shear which tend to direct the tab member 42 and the slot member 44 apart.

If desired, the tab member 42 can be disconnected from the slot member 44 by pulling the tab member 42 further from the slot member 44 and aligning the proximal edge 60 of the tab member 42 with the slot 46. Next, the proximal edge 60 of the tab member is pulled through the slot 46 followed by the distal edge 62. Because the tab member 42 can be connected to the slot member 44 and subsequently disconnected from the slot member 44 without tearing or breakage, the fastening device is said to provide a releasable connection between the tab member 42 and the slot member 44.

Referring to FIG. 11, the absorbent articles 20 can be formed into a pant by fastening the tab and slot members 42 and 44, and packaging the fastened articles 20 into any suitable packaging 101. The term "pre-fastened" is thus intended to refer to an absorbent article having fastening elements that have been fastened to define a pant-like garment, prior to packaging the article, such that the user receives a pant-like garment that can be applied to the wearer without having to fasten the fastening elements. Accordingly, the user need only apply the articles 20 to the lower torso region of the wearer. It should be appreciated, however, that in many instances, for example when applying a given article 20 to a standing wearer, the user may decide to unfasten the tab member 42 from the slot member 44, apply the article 20, and subsequently refasten the tab and slot members 42 and 44.

As described above, the present invention recognizes that the fastening devices 41 should be substantially rigid prior to and while engaging the tab member 42 in the slot member 44 in order to ensure that the fastening system 40 is reliably fastened. Furthermore, in order to limit the ability of the fastening devices 41 to press into the abdomen or other bodily area of the wearer and cause discomfort and/or skin marking and/or irritation, at least one of the tab member 42 and slot member 44 constructed in accordance with the present invention has a stiffness that is at a first level during fastening of the fastening device 41, and that can be reduced to a second level that is less than the first level during use. The first stiffness level is sufficiently high to ensure reliable connection between the tab member 42 and slot member 44, while the second stiffness level is high enough to prevent the fastening device 41 from unintentionally disengaging, but low enough to limit the ability of the tab member 42 and/or slot member 44 to press into the wearer's body and cause discomfort and/or skin marking and irritation.

The fastening device 41 can be responsive to one or more predetermined stimuli that cause the desired stiffness reduction. The stimuli can be internal or external to the absorbent article, and can include any one or more of, for example, an applied force, a thermal fluctuation, and a change in humidity or liquid presence.

Figure 12A:
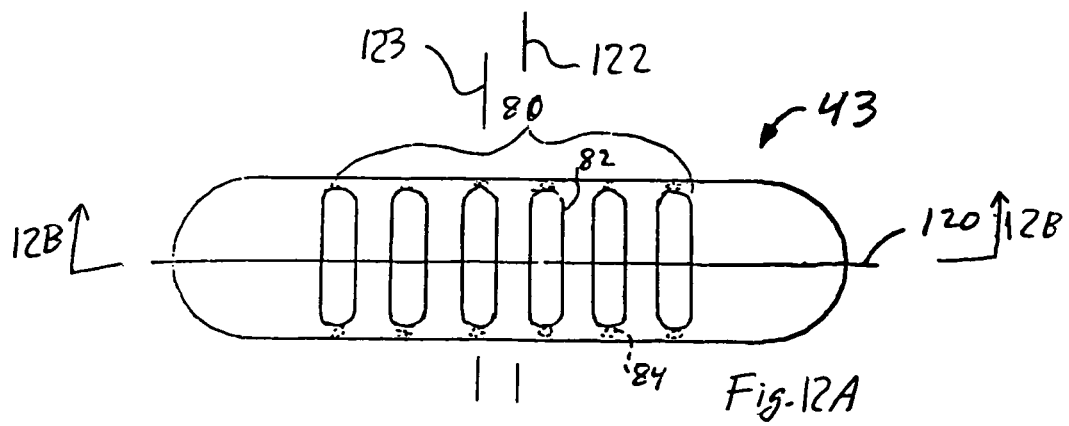
FIG. 12A is a top plan view of a tab element forming part of the tab member incorporating an integral variable stiffness member constructed in accordance with one embodiment of the present invention.

Referring now to FIG. 12A, the stiffness of the fastening device 41 is controlled with a variable stiffness member 80, associated with the device 41, that undergoes a reduction in stiffness in response to a predetermined stimulus. The variable stiffness member 80 can be integral with any of the fastening device members (i.e., the tab member 42 and/or slot member 44 that make up the fastening device 41), or can be external to the fastening device members.

In the embodiment illustrated in FIG. 12A, the variable stiffness member 80 is integrated in the tab element 43 and has at least one property that differs from the remainder of the tab element 43, thereby rendering the tab member 42 capable of reducing its stiffness from an original stiffness level to a reduced stiffness level in response to a predetermined stimulus. In accordance with certain aspects of the present invention, the stiffness is reduced by a percentage of the original stiffness that is within a range defined at its lower end by and between 10%, 20%, 30%, 40%, and 50%, and defined at its upper end by and between 80%, 90%, 99%, and up to 100%. The stiffness reduction of the variable stiffness member 80 thus reduces the overall stiffness of the corresponding fastening device 41.

The variable stiffness member 80 comprises a geometric configuration of the tab element 43 that induces plastic deformation (and hence stiffness reduction) in response to one or more forces applied to the variable stiffness member 80.

Specifically, in one embodiment, the variable stiffness member 80 includes one force transfer zone 82. Alternatively, any suitable number (e.g., 2, 3, 4, 5, 6, etc. . . . ) of force transfer zones 82 are formed in the tab element 43. The force transfer zones 82 can be arranged adjacent each other in a direction along the length of the tab element 43 (i.e., along axis 120). Each force transfer zone 82 can extend substantially parallel to the lateral axis 122 as illustrated in FIG. 12A, or each force transfer zone 82 can extend in a direction that is offset from any axis that defines tab element 43. Alternatively, one or more force transfer zones 82 can extend substantially parallel to the lateral axis 122, while other force transfer zones extend along a direction that is angularly offset from the lateral axis 122 (and from their adjacent force transfer zone 82).

Figure 12B:
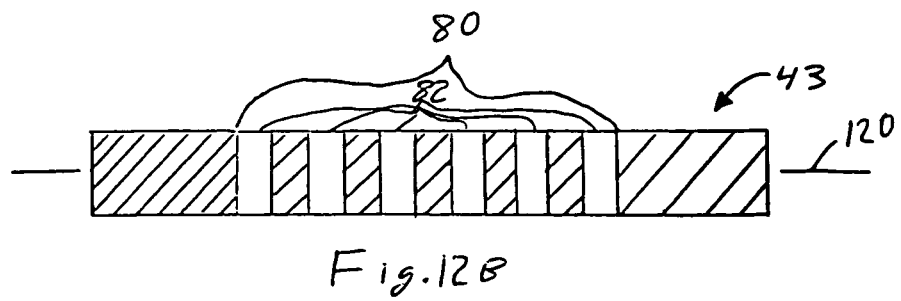
FIG. 12B is an enlarged schematic sectional side elevation view of the tab member illustrated in FIG. 12A taken along line 12B-12B.

As illustrated in FIG. 12B, the force transfer zones 82 can comprise apertures extending through the tab member 42. In other embodiments, the force transfer zones 82 do not extend completely through the tab member, but instead are recessed in the tab member 42 as illustrated in FIG. 12C.

Figure 12C:
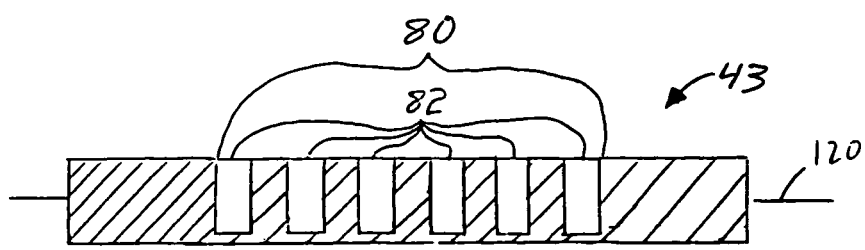
FIG. 12C is a schematic sectional side elevation view of the tab member similar to FIG. 12B but constructed in accordance with an alternative embodiment.
Figure 12D:
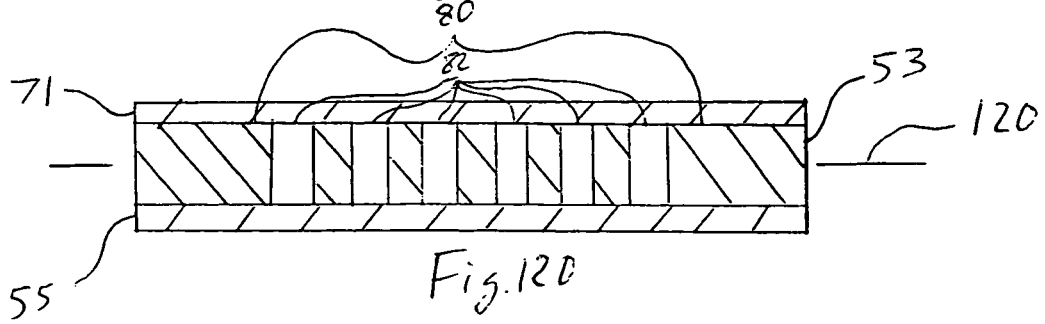
FIG. 12D is a schematic sectional side elevation view of the tab member similar to FIG. 12B but constructed in accordance with an alternative embodiment.

One skilled in the art will appreciate that the force transfer zones 82 illustrated in FIGS. 12B and 12C are illustrated schematically, and that the zones 82 can extend through or partially through any of the layers that comprise the tab element 43 as illustrated and described above with reference to FIG. 8. Alternatively, the force transfer zones 82 can extend through or partially through any combination of layers that comprise the tab element 43 as illustrated in FIG. 8. For instance, as illustrated in FIG. 12D, the force transfer zones 82 extend through the core member 53 of the tab element 43, and are completely contained in the tab element 43.

With continuing reference to FIGS. 9 and 12A, during operation when the user first connects the tab member 42 to the slot member 44, the tab member 42 is relatively stiff as the deformation zones 84 have not yet experienced the force necessary to cause plastic deformation. Accordingly, the tab member 42 and the slot member 44 will readily mate together. However, as the user manipulates the components of the fastening system 40, the tab member 42 is likely to experience a force and impart the force onto tab element 43, core member 53, and variable stiffness member 80, thereby causing the core member 53 to plastically deform at one or more of the deformation zones 84.

In accordance with one aspect of the present invention, a force within the range of 50 g and 1.5 kg, and alternatively within the range of 50 g and 500 g, can be sufficient cause the desired stiffness reduction. This force can be a compressive force about any axis passing through the tab member 42, it being appreciated that in practice the tab member 42 will be out of plane with the compressive force, thus resulting in a bending force applied to the tab member 42. Alternatively, a direct bending force can be applied to tab member 42. While at least some of the above-described variable stiffness members 80 can be activated in response to the bending force $F_b$ about the lateral axis 122 (or about a bending axis that can be substantially parallel to, or coinciding with, the lateral axis 122), one having ordinary skill in the art will appreciate that any suitable bending force could activate the variable stiffness members, such as a bending force $F_b'$ about the longitudinal axis 120 (or about a bending axis that can be substantially parallel to, or coinciding with, the longitudinal axis 120), and a bending force $F_b''$ about a z-axis 124 extending orthogonal to both the lateral axis 122 and the longitudinal axis 120 (or about a bending axis that can be substantially parallel to, or coinciding with, the z axis 124). It should be further appreciated that the forces can be applied indirectly to the variable stiffness member 80 via, for example, the tab member 42, the absorbent article 20, or any other intermediate member capable of receiving, either directly or indirectly, a force and applying the force to the variable stiffness member 80. As illustrated in FIG. 12A, a bending axis 123 is illustrated as extending parallel to the lateral axis 122.

The amount of force required to cause plastic deformation can be determined by numerous factors, including the material properties (e.g., Young's modulus, yield point, ultimate tensile strength, and ductility), the size and shape of the force transfer zones 82, the number of force transfer zones 82, and the thickness of the tab element 43. For instance, materials having a Young's modulus within the range of 0.25 GPa and 3.0 GPa have been determined to be acceptable.

In accordance with one aspect of the present invention, plastic deformation, and the resultant suitable stiffness reduction, occurs after five or fewer deformation cycles, alternatively three or fewer deformation cycles, and alternatively still one deformation cycle. Methods that can be used to determine whether the stiffness has been sufficiently reduced after a given deformation cycle is described in more detail below with reference to FIGS. 21A-B.

Certain aspects of the invention provide a stiffness reduction of the core member 53, tab element 43, and tab member 42 when the article 20 is worn. Alternatively, if the user fails to apply the requisite force while connecting the tab member 42 and slot member 44, the body movement of the wearer, for instance leg and/or waist movement, will apply one or more requisite forces to the tab element 43 necessary to cause plastic deformation of the variable stiffness member 80 and, hence, a corresponding reduction in tab member stiffness. Consequently, tab member 42 is less likely to press into the wearer's body than tab member 42 would otherwise be if the stiffness was not reduced.

Figure 13A:
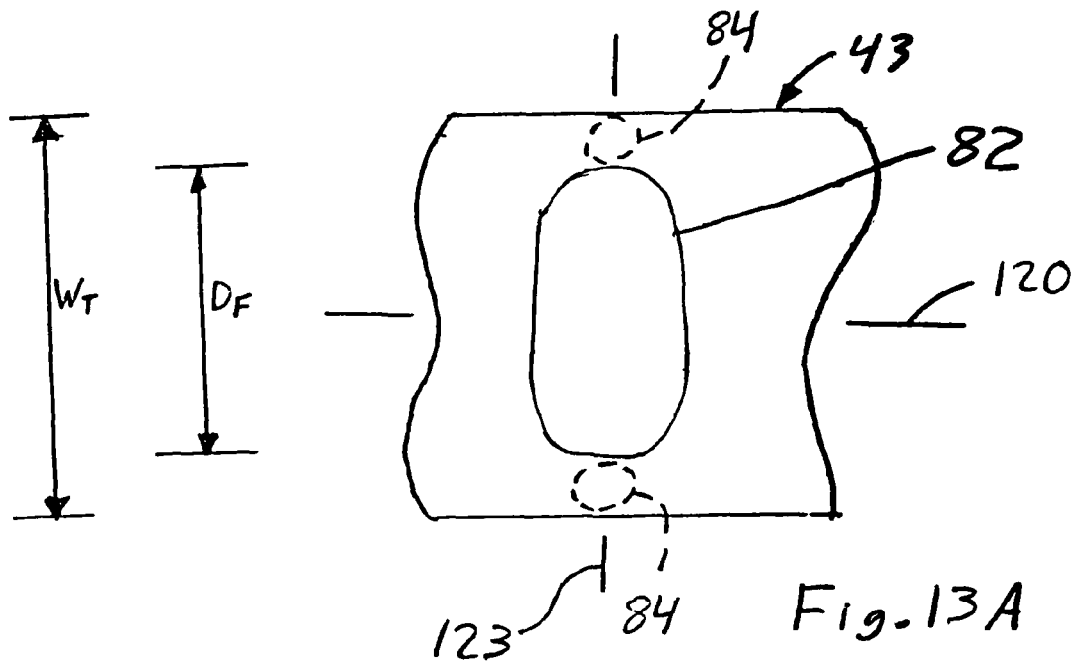
FIG. 13A is an enlarged top plan view of a portion of the tab member illustrated in FIG. 12A.

Referring now to FIG. 13A, an enlarged portion of the tab element 43 is illustrated showing a force transfer zone 82 and the corresponding deformation zones 84 disposed between the force transfer zone 82 and the periphery of the tab element 43. As illustrated, the force transfer zone 82 extends along a direction substantially parallel to the bending axis 123, which in turn can extend substantially parallel to, or can coincide with, lateral axis 122. The tab element 43 defines width $W_T$ extending substantially along, or parallel to, the bending axis 123, while the force transfer zone 82 defines a distance $D_F$ along the axis 123 that is at least 50%, alternatively at least 60%, alternatively at least 75%, and alternatively at least 90%, of the width $W_T$ of the tab element 43. Accordingly, the deformation zones 84 define a cumulative distance (as defined below) extending along, or parallel to, the bending axis 123 that is less than 50%, alternatively less than 40%, alternatively less than 25%, and alternatively less than 10% the tab element width $W_T$.

Figure 13B:
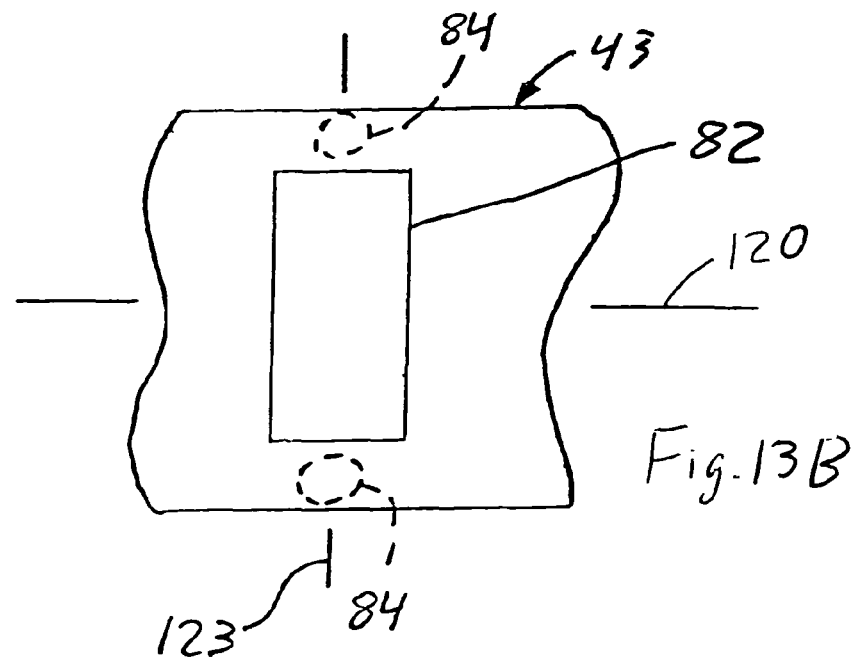
FIG. 13B is a top plan view similar to FIG. 13A but constructed in accordance with an alternative embodiment.

Referring to FIG. 13B, it should appreciated that the force transfer zone 82 can comprise any geometric configuration that produces a suitable deformation zone 84. Suitable shapes include a rectangle as illustrated, and alternatively with a square, triangle, circle, oval, slit, notch, and the like, or combinations thereof.

Figure 13C:
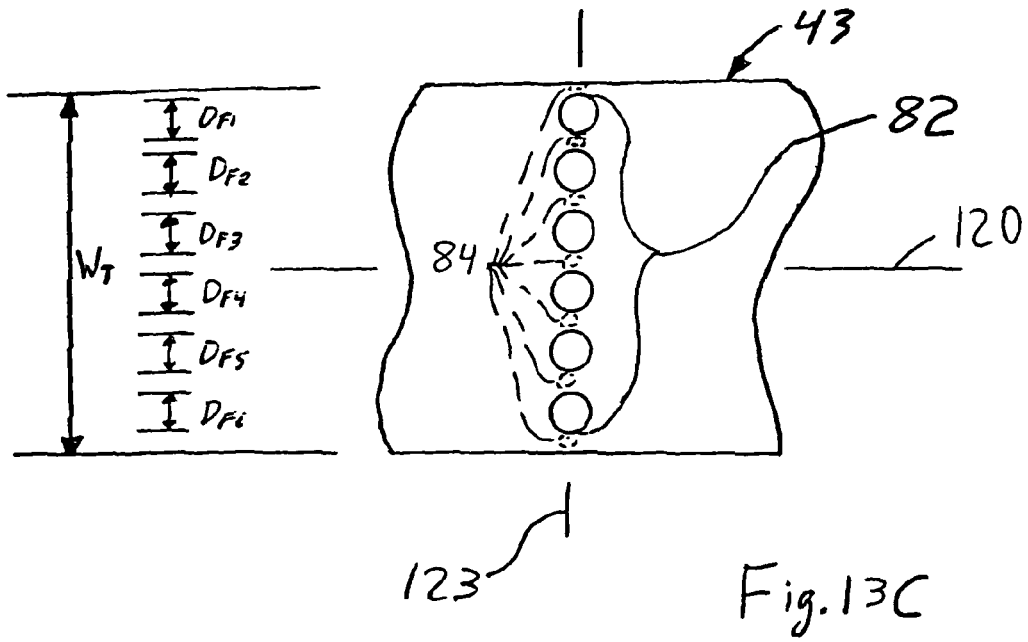
FIG. 13C is a top plan view similar to FIG. 13A but constructed in accordance with another alternative embodiment.

Referring now to FIG. 13C, the tab element 43 can include a plurality of force transfer zones 82 extending along the bending axis 123. The force transfer zones 82 define a corresponding plurality of deformation zones 84 interposed between force transfer zones 82, and between the outermost force transfer zones 82 and the periphery of tab element 43. Each force transfer zone 82 defines a distance $D_{FN}$ extending along (or parallel to) the bending axis 123, wherein N corresponds to the number of force transfer zones. As illustrated, N=6. The cumulative distance of $DF_{1...N}$ (defined as the sum the individual distances of $DF_1 \ldots D_{FN}$) is at least 50%, alternatively at least 60%, alternatively at least 75%, and alternatively at least 90%, of the width $W_T$ of the tab element 43. Accordingly, the deformation zones 84 define a cumulative distance extending along, or parallel to, the bending axis 123 that is less than 50%, alternatively less than 40%, alternatively less than 25%, and alternatively less than 10% the tab element width $W_T$.

Figure 14:
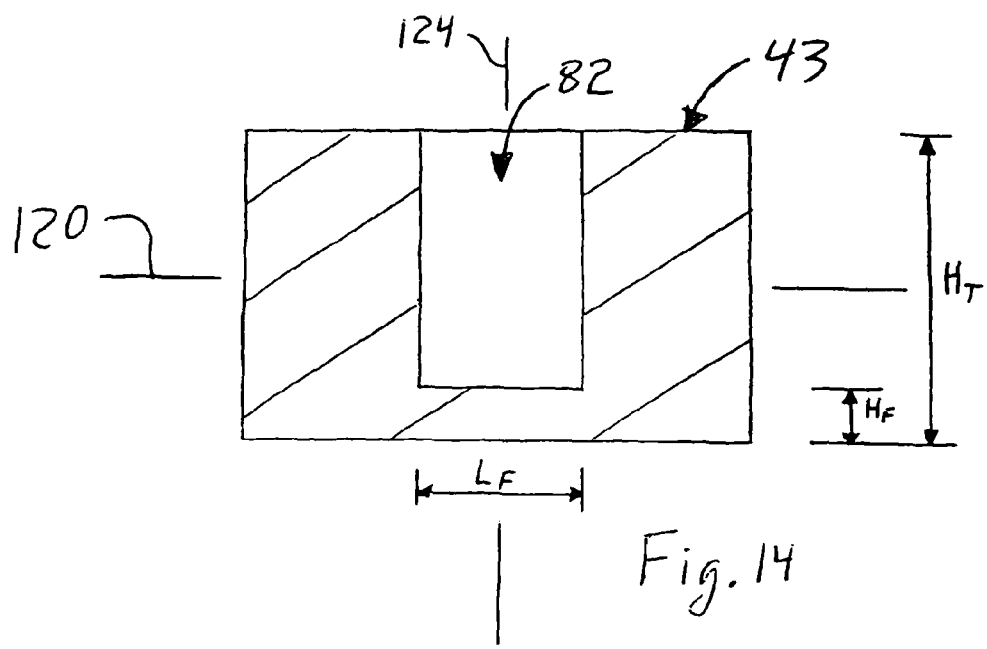
FIG. 14 is an enlarged sectional side elevation view of a portion of the tab member as illustrated in FIG. 12C.

Referring now to FIG. 14, the force transfer zone 82 of FIG. 12C defines a length $L_F$ extending in a direction perpendicular to the bending axis 123 illustrated in FIG. 12A (e.g., parallel to the longitudinal axis 120). Furthermore, the tab element 43 defines a height $H_F$ at the force transfer zone 82 that is substantially less than the height $H_T$ of the tab element 43 at a location adjacent the force transfer zone 82. In accordance with certain aspects of the present invention, the tab element 43 has an average height $H_F$ along at least 50% of the length $L_F$ of the force transfer zone that is no greater than 50%, alternatively no greater than 40%, alternatively no greater than 25%, and alternatively no greater than 10% relative to the tab element height $H_T$ of adjacent the force transfer zone 82.

During operation, when a force is applied to the tab member 42 and, hence, the variable stiffness member 80, the force transfer zones 82 transfer the received forces to a plurality of stress concentration zones which, in turn, establish schematically illustrated deformation zones 84 configured to plastically deform in response to the requisite applied forces. The deformation zones 84 as illustrated are disposed at locations disposed proximal the lateral ends of the force transfer zones 82 between the force transfer zones 82 and the periphery of the tab element 43. The deformation zones 84 define regions in tab member 42 that receive applied forces from the force transfer zones 82 and are, in turn, configured to undergo plastic deformation. In particular, the deformation zones 84 are configured to plastically deform upon application of relatively low forces, such as the forces required to attach the tab member 42 to slot member 44, or the forces imparted on the tab element 43 by the wearer's body as the article 20 is worn (i.e., after the fastening system 40 has been fastened).

One having ordinary skill in the art will appreciate that the number of force transfer zones 82 and deformation zones 84, and ratio of force transfer zones 82 to deformation zones 84 can increase or decrease, and that the ratio of force transfer zones 82 to deformation zones 84 could likewise increase or decrease relative to the illustrated embodiments.

Figure 15:
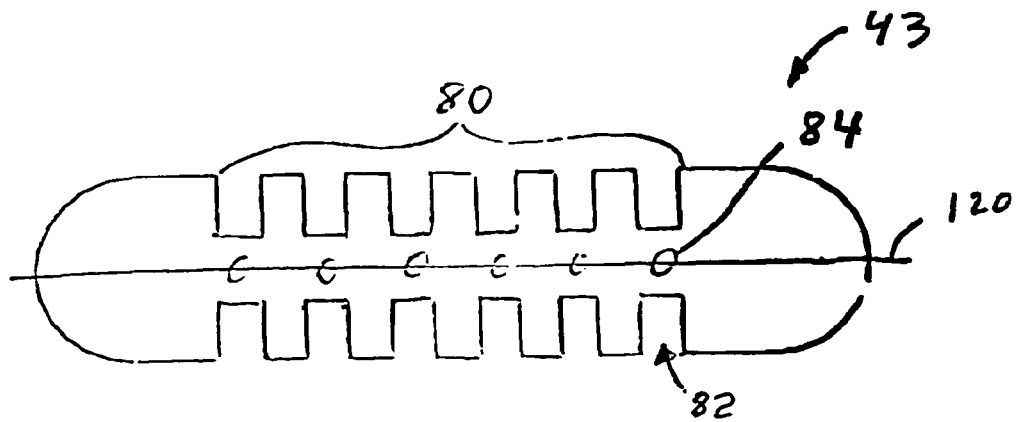
FIG. 15 is a top plan view of the tab element incorporating an integral variable stiffness member constructed in accordance with an alternative embodiment.

While the force transfer zones 82 have been illustrated as being formed within the confines of the periphery of the tab element 43, it should be appreciated that the periphery of the tab element 43 can, at least in part, define the force transfer zones 82. For instance, referring to FIG. 15, the force transfer zones 82 are formed in the tab element 43 and extend laterally inwardly from both longitudinally extending outer edges of the tab element 43. Opposing force transfer zones 82 are laterally aligned and stop short of each other such that deformation zones 84 are formed between the opposing force transfer zones 82 substantially along the longitudinal axis 120.

Figure 16:
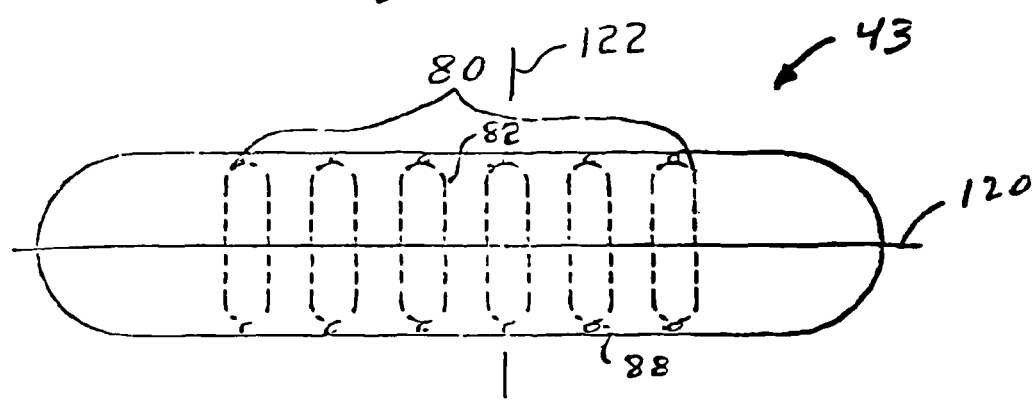
FIG. 16 is a top plan view of the tab element incorporating an integral variable stiffness member constructed in accordance with another alternative embodiment.

Referring now to FIG. 16, the variable stiffness member 80 constructed in accordance with an alternative embodiment comprises a geometric configuration of tab member 42 that induces a fracture in response to one or more forces applied to the tab member 42. The member 80 includes a plurality of force transfer zones 82 formed in the tab element 43 that create a corresponding plurality of stress concentrations that provide fracture zones 88 at locations disposed proximal the force transfer zone ends between the force transfer zones 82 and the periphery of the tab element 43. Specifically, the fracture zones 88 define regions in tab element 42 that are configured to fail at relatively low forces (e.g., between 50 g and 1.5 kg or, alternatively, between 50 g and 500 g). In accordance with certain aspects of the present invention, the stiffness of the fracture zones 88 is reduced by a percentage of the original stiffness that is within a range defined at its lower end by and between 10%, 20%, 30%, 40%, and 50%, and defined at its upper end by and between 80%, 90%, 99%, and up to and including 100%. As described above with reference to FIG. 13A, the force transfer zones 82 and the corresponding fracture zones 88 occupy a percentage distance across the tab element 43 in a direction substantially parallel to the bending axis 123. Whether the variable stiffness member 80 defines fracture zones 88 or deformation zones 84 can be determined, for instance, based on the material properties of the variable stiffness member 80, it being appreciated that materials having lower ductilities are more likely to fracture while materials having higher ductilities are more likely to undergo deformation.

While the force transfer zones 82 are laterally extending and oval-shaped as illustrated, the force transfer zones 82 can alternatively assume any size and/or shape (e.g., slits, holes, notches, shaved areas of reduced thickness, etc. . . . ) and that one or more force transfer zones 82 can be formed in tab element 43 at any suitable location and in any suitable configuration to effect a desired localized fracture zone 88 (e.g., see FIGS. 12-15).

During operation, when the user (who can be the wearer or a caregiver) first connects the tab member 42 to the slot member 44 when fastening an absorbent article onto the body of the wearer, the tab member 42 is relatively stiff as the tab member 42 retains its original stiffness. Accordingly, the tab member 42 and the slot member 44 will readily mate together. The user can then apply the predetermined stimulus to the fastening system 40 and, hence, the variable stiffness member 80, for example by manipulating the components of the fastening system 40. The tab element 43 is thus likely to experience a force that causes the tab member 42 to fail at one or more of the fracture zones 88 and/or deformation zones 84, thereby effecting a reduced variable stiffness member stiffness, and consequently a reduced tab element stiffness and, accordingly, a reduced fastening system stiffness as the article 20 is worn. Alternatively, if the user fails to apply the requisite force while connecting the tab member 42 and slot member 44, the body movement of the wearer, for instance leg and/or waist movement, will apply the force that causes failure and a reduction in tab member stiffness. Consequently, tab member 42 has a reduced likelihood of pressing into the wearer's body.

One skilled in the art will further appreciate that core member 53 could be formed from a hybrid material whose ductility varies along the core member 53, or that stronger bending forces may occur at some locations on core member 53 with respect to the remainder of the core member 53. Consequently, the core member 53 may include both deformation zones 84 and fracture zones 88.

Figure 17A:
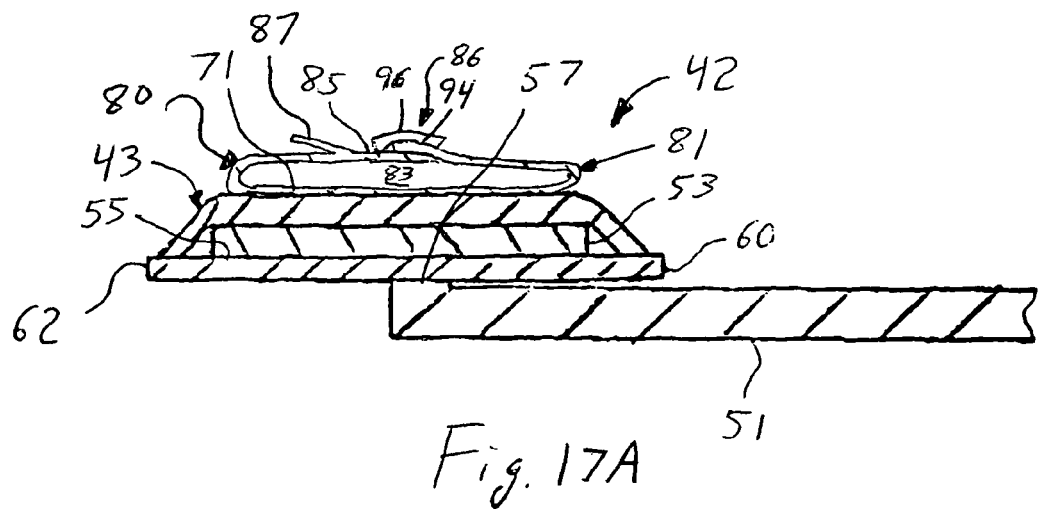
FIG. 17A is a schematic end view of a fastening device incorporating a variable stiffness member in the form of a deflatable bladder.
Figure 17B:
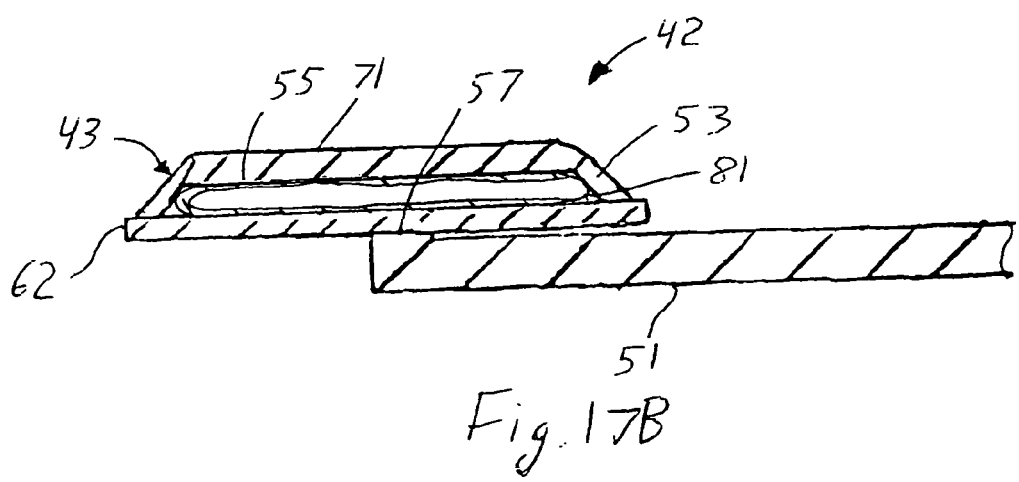
FIG. 17B is a schematic end view of a fastening device incorporating the deflatable bladder in accordance with an alternative embodiment.

Referring now to FIG. 17A, the variable stiffness member 80 can comprise a member whose stiffness is responsive to fluctuations in internal fluid pressure. For instance, the variable stiffness member 80 can comprise an enclosed bladder 81 that resides on an outer surface of the tab element 43. As illustrated, the bladder 81 is disposed on the upper surface of the tab element 43 (i.e., the second substrate layer 71), though it should be appreciated that the bladder 81 could reside anywhere on the tab element 43 such that the bladder 81 can be deflated to yield a desired stiffness reduction. Alternatively, as illustrated in FIG. 17B, the bladder 81 can be encapsulated by the tab element 43. Specifically, as illustrated, the bladder 81 has replaced the core member 53 shown in FIG. 8. Alternatively, the bladder 81 can replace any tab element layer, or be disposed between any tab element layers.

The bladder 81 defines an internal void 83 that can be maintained at an internal pressure that causes the bladder 81 to have a stiffness that is sufficiently high to facilitate an interconnection between the tab member 42 and the slot member 44. The internal pressure can be provided via a volume of fluid (e.g., gas, liquid such as water, gel, or the like) or small loose particles such as sand or the like. The stiffness of the bladder 81 is then reduced upon a decrease in the internal pressure.

The decreased internal pressure can be effected by one of several mechanisms. For instance, the bladder 81 may rupture in response to the application of an external pressure, for instance by the user by squeezing the bladder, bending the tab element 43 (and thus the bladder 81), or by rupturing the bladder 81 with any suitable sharp object, such as a pin 79.

Figure 17C:
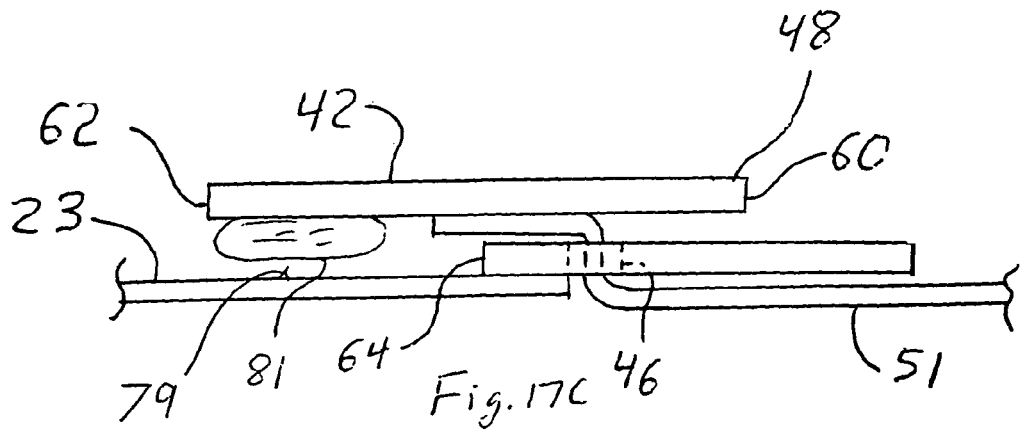
FIG. 17C is a schematic end view of a fastening device incorporating the deflatable bladder in accordance with an alternative embodiment.

For instance, referring to FIG. 17C, once the tab member 42 and the slot member 44 have been fastened, the bladder 81 is positioned between the tab member 42 and the ear that carries the slot member 44 (the front ear 23 as illustrated). Specifically, the bladder 81 is attached to the undersurface of the tab member 42 adjacent the distal edge 62 via any suitable mechanism such as an adhesive, cohesive, mechanical fastener, or fusion bond. A pin 79 can be also disposed between the tab member 42 and the front ear 23 in juxtaposition with the bladder 81 such that depressing the tab member 42, adjacent the distal edge 62, against the front ear 23 will cause the pin 79 to penetrate and rupture the bladder 81. The pin 79 can protrude slightly upward from the front ear 23 as illustrated, or downward from the tab member 42 in the manner illustrated in FIG. 17D. Alternatively, the bladder 81 can be attached to the upper surface of the front ear 23 in alignment with the tab member 42 adjacent the distal edge 62.

Figure 17D:
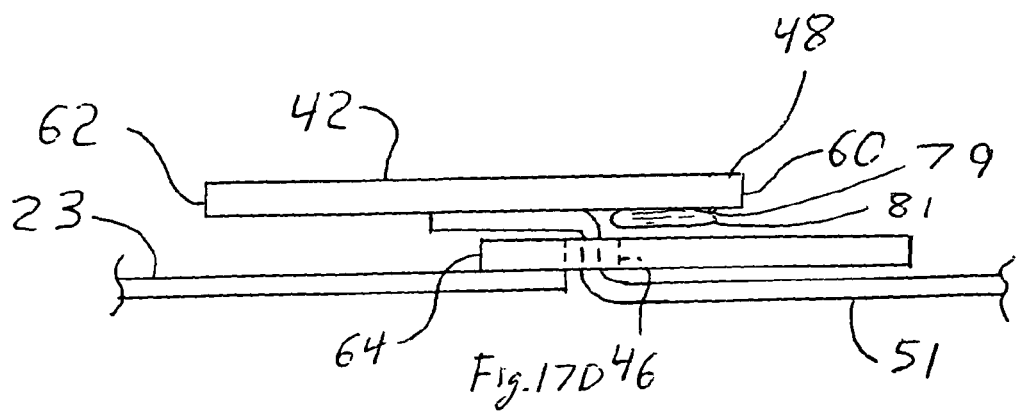
FIG. 17D is a schematic end view of a fastening device incorporating the deflatable bladder in accordance with an alternative embodiment.

Referring now to FIG. 17D, the bladder 81 is positioned between the tab member 42 and the slot member 44. Specifically, the bladder 81 is attached to the undersurface of the tab member 42 adjacent the proximal edge 60 via any suitable mechanism such as an adhesive, cohesive, mechanical fastener, or fusion bond. The pin 79 can be also disposed between the tab member 42 and the slot member 44 in juxtaposition with the bladder 81 such that depressing the tab member 42, adjacent the proximal edge 60, against the slot member 44 will cause the pin 79 to penetrate and rupture the bladder 81. The pin 79 can protrude slightly downward from the tab member 42 as illustrated, or upward from the slot member 44 in the manner illustrated in FIG. 17C. Alternatively, the bladder 81 can be attached to the upper surface of the slot member 44 in alignment with the tab member 42 adjacent the proximal edge 60.

Figure 17E:
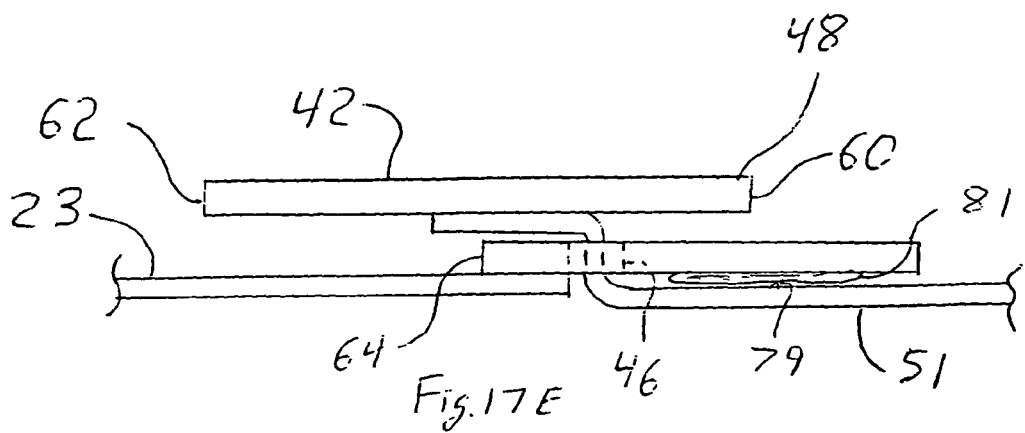
FIG. 17E is a schematic end view of a fastening device incorporating the deflatable bladder in accordance with an alternative embodiment.

Referring now to FIG. 17E, the bladder 81 is positioned between the slot member 44 and the substrate carrier 51. Specifically, the bladder 81 is attached to the undersurface of the slot member 44 and aligned with the substrate carrier 51 via any suitable mechanism such as an adhesive, cohesive, mechanical fastener, or fusion bond. The pin 79 can be also disposed between the slot member 44 and the substrate carrier 51 in juxtaposition with the bladder 81 such that depressing the slot member 44 will cause the pin 79 to penetrate and rupture the bladder 81. The pin 79 can protrude upward from the substrate carrier 51 as illustrated, or slightly downward from the slot member 44 in the manner described above. Alternatively, the bladder 81 can be attached to the upper surface of the substrate carrier in alignment with the slot member 44.

Referring now to FIG. 17F, the bladder 81 is attached to the undersurface of the front ear 23 such that the bladder 81 is in at least partial vertical alignment with the tab member 42 adjacent the distal edge 62. The pin 79 protrudes downward from the front ear 23 in juxtaposition with the bladder 81. Accordingly, when the front ear 23 is bent or otherwise pressed against the bladder 81, the pin 79 can penetrate and rupture the bladder 81, thereby decreasing the internal bladder pressure.

Referring now to FIG. 17G, the bladder 81 is attached to the undersurface of the substrate carrier 51 such that the bladder 81 is in at least partial vertical alignment with the tab member 42 and slot member 44. The pin 79 protrudes downward from the substrate carrier in juxtaposition with the bladder 81. Accordingly, when the substrate carrier is bent or otherwise pressed against the bladder 81, the pin 79 can penetrate and rupture the bladder 81, thereby decreasing the internal bladder pressure.

While the bladder 81 as positioned in FIGS. 17F-G is not directly attached to the fastener elements (e.g., tab 42 and slot 44), the bladder 81 is nonetheless operatively associated with the fastening device. The term "operatively associated with" is used herein to refer to the ability of the variable stiffness member 80 to affect the stiffness of one or more fastener elements (i.e., tab member 42 and/or slot member 44), and thus the fastening device 41. As illustrated in FIGS. 17F-G, the present inventors have found that the variable stiffness member 80 can be operatively associated with the fastening device 41 (and hence the fastening system 40) if it is at least in partial vertical alignment with any of the fastener elements.

FIGS. 17A-G illustrate various embodiments whereby the variable stiffness member 80 is attached to a lower surface of the tab member 42, the slot member 44, and the elements that support the tab and slot members 42 and 44 (i.e., the substrate carrier 51 and the front ear 23). It should be appreciated that any of the external variable stiffness members 80 described herein can be positioned so that they are operatively associated with the fastening system 40 in the manner illustrated in FIGS. 17A-G.

It should further be appreciated that, if the bladder 81 retains a liquid or gel, the leakage of material from the void 83 can cause wetness of surrounding tab member materials and decrease the stiffness of the tab element 43 if, for instance, the tab element 43 includes a humidity-responsive variable stiffness member as described in more detail below.

Alternatively or additionally, the bladder 81 can include a frangible zone 85 that is connected to a tab 87 extending outward from the bladder 81. A user can then pull on the tab 87 and separate the frangible zone 85 from the remainder of the bladder, thus producing a flow path for the pressurized contents escape from the void 83. Alternatively still, or additionally, a release valve 86 can be provided on the bladder 81 which, in accordance with one embodiment, comprises a flap 94 that is folded over and held in place by a removable material, such as an adhesive layer 96. Once the adhesive layer 96 is removed, the flap 94, along with a corresponding aperture, is exposed that enables the flow of pressurized contents from the void 83 into the ambient environment.

Figure 18:
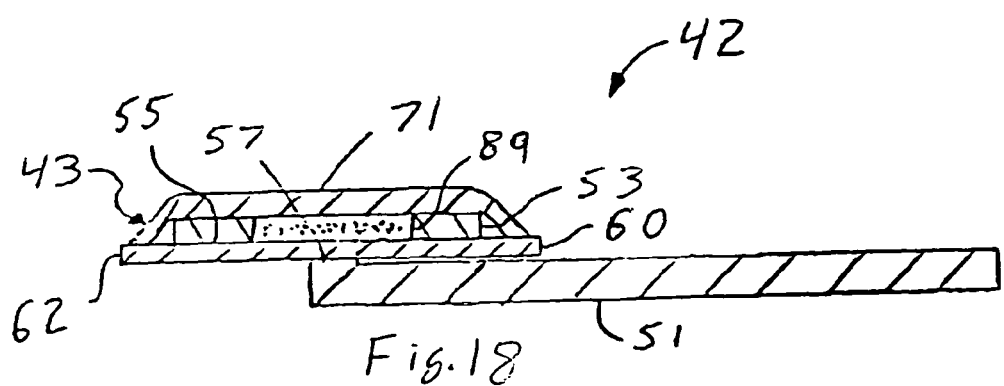
FIG. 18 is sectional side elevation view of the tab member incorporating an integral variable stiffness member constructed in accordance with one embodiment.

Referring now to FIG. 18, an integral variable stiffness member 80 constructed in accordance with an alternative embodiment is a layer 89 that provides at least a portion 89 of the tab element 43. In the illustrated embodiment, the layer 89 is integrated with the core member 53 and is formed from a material or combination of materials different from that of the surrounding core member 53. Alternatively, the variable stiffness member 80 comprises an additive material or combination of materials that is intermixed with at least a portion or all of at least one of the tab element components (e.g., core member 53).

Figure 19A:
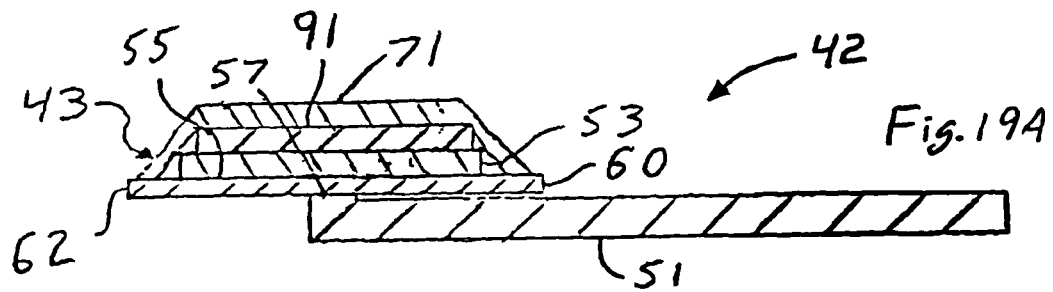
FIG. 19A is a sectional side elevation view of the tab member incorporating an external variable stiffness member constructed in one embodiment.
Figure 19B:
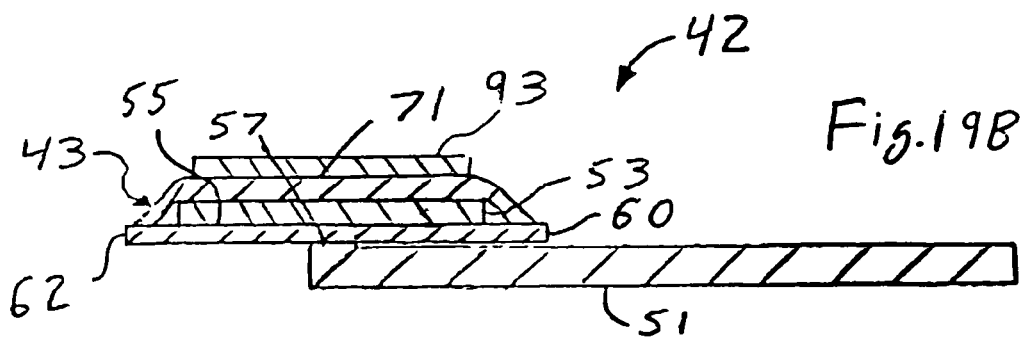
FIG. 19B is a sectional side elevation view of the tab member incorporating an external variable stiffness member constructed in accordance with an alternative embodiment.

Alternatively, the variable stiffness member 80 can be an external member attached to, or co-extruded with, the core member 53 at any desirable location. For instance, referring to FIG. 19A, the variable stiffness member 80 is a layer 91 attached to tab member 42 at a location between the core member 53 and the second substrate layer 71. Alternatively, as illustrated in FIG. 19B, the variable stiffness member 80 is a layer 93 attached to the upper surface of the second substrate layer 71. The other tab member components can have a relatively low stiffness compared to the original stiffness of the tab member 42 such that the overall stiffness of the core member 53 is substantially regulated by the variable stiffness member 80.

Figure 20:
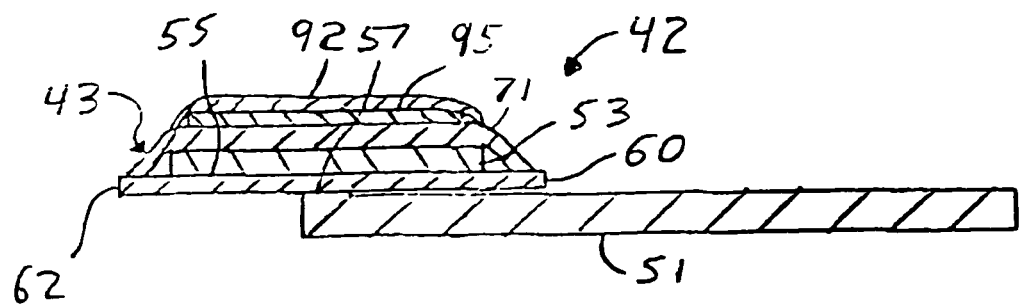
FIG. 20 is a sectional side elevation view of the tab member incorporating an external variable stiffness member constructed in accordance with another alternative embodiment.

Alternatively, as illustrated in FIG. 20, an alternative embodiment of an external variable stiffness member 80 can be a layer 95 that is encased by a nonwoven or other suitable layer 92 that is, in turn, attached to the tab element 43, for example to the upper surface of second substrate layer 71 so as to be exposed to the user. The variable stiffness member 80 can extend along a length that is less than, substantially equal to, or greater than the length of the tab element 43. Because the encasement layer 92 is exposed to the user, the user can be prompted to apply a force to the variable stiffness member 80 while connecting the fastening system 40 to ensure that the tab member 42 will be sufficiently flexible while the article 20 is worn. Furthermore, with the variable stiffness member 80 disposed on the outer surface of second substrate layer 71 (or other tab element outer surface), the variable stiffness member 80 can provide both tactile and visual feedback to the user once the variable stiffness member 80 has failed. The web 92 encases the brittle material and prevents the user/wearer from exposure to loose fragments once the variable stiffness member 80 has sufficiently failed.

One skilled in the art will appreciate that region 89 and layers 91, 93, and 95 can be geometrically configured to define deformation zones 84 and/or fracture zones 88 in the manner described above.

In accordance with certain aspects of the invention, the variable stiffness member 80, whether integral or external, can comprise a material or combination of materials having various properties that will effect a desired stiffness reduction.

For instance, the variable stiffness member can be ductile and/or has a hysteresis (i.e., undergoes plastic deformation) in response to five or fewer deformation cycles, alternatively three or fewer deformation cycles, and alternatively still one deformation cycle. Examples of such materials include plastics, films, foams, nonwoven webs, woven webs, paper, laminates, steel, fiber reinforced plastics, lead, aluminum, and the like, or combinations thereof. The material hysteresis results in a reduction in stiffness of the material and, hence, the tab element 43 and tab member 42 when a requisite force is applied to the variable stiffness member 80. The plastic deformation creates a permanent change in the properties and shape at the region of deformation of the tab element 43 such that the tab element 43 is unable to return to its original stiffness once the bending force is applied to the tab element 43, thereby reducing the overall stiffness of tab element 43 and tab member 42 and allowing the tab member 42 to more easily conform to the outer body surface of the wearer.

In accordance with an alternative embodiment, the variable stiffness member 80 is responsive to thermal fluctuations. Specifically, the material stiffness-dependent properties, such as Young's modulus, yield point, and ultimate tensile strength, can vary in response to the temperature of the material. In certain aspects of the invention, the thermally responsive variable stiffness member 80 undergoes a stiffness reduction at temperatures above ambient temperature and below body temperature. Examples of suitable temperatures can therefore be within a range of about 86° and 98.6° Fahrenheit, and alternatively within the range of about 89.6° and 95° Fahrenheit. The stiffness can be reduced by a percentage of the original stiffness that is within a range defined at its lower end by and between 10%, 20%, 30%, 40%, and 50%, and defined at its upper end by and between 80%, 90%, 99%, and up to 100%.

Examples of such temperature-responsive materials include any material that softens or changes phase (e.g., solid to liquid, or solid to crystalline) in the above-disclosed temperature ranges. Examples are phase change solvents of the type disclosed in U.S. Patent Publication No. 2004/0021130 published on Feb. 5, 2004 to Steven D. Smith, et al.

Additional examples of suitable temperature-responsive materials include polymers having an order-disorder transition temperature (a temperature at which the modulus decreases from an initial level). The order-disorder transition temperature can be set where desired by varying the polymer composition and/or molecular weight as is known by one having ordinary skill in the art. General examples include block copolymers having hard and soft segments. While such block copolymers are known in the art as having relatively high order-disorder transition temperatures, they can be reformulated for transition temperatures within the above-identified range as desired. The block co-polymer may be di-block, tri-block, or other number of blocks in which at least one block is styrene and at least one other block is either isoprene or butadiene. Alternatively, at least one block is styrene and some of the other blocks are isoprene and yet other blocks are butadiene.

Exemplary block copolymers may include styrene-diene-styrene or styrene-olefin-styrene triblock copolymers such as styrene-butadiene-styrene (S-B-S), styrene-ethylene/butylene-styrene (S-EB-S), styrene-ethylene/propylene-styrene (S-EP-S), styrene-isoprene-styrene (S-I-S), hydrogenated polystyrene-isoprene/butadiene-styrene (S-IB-S), and mixtures thereof. Commercially available block copolymers include KRATON® from the Shell Chemical Company, Huston, Tex.; SEPTON® from Kuraray America, Inc. New York, N.Y., and VECTOR® from Dexco Chemical Company, Houston, Tex.

Certain embodiments of the present invention further contemplate block copolymers having more than one A block and/or more than one B block, wherein each A block may be derived from the same or different vinylarene monomers and each B block may be derived from the same or different olefinic monomers.

The block copolymers may also be radial, having three or more arms, each arm being a B-A, B-A-B-A, or the like type copolymer and the B blocks being at or near the center portion of the radial polymer.

Tapered block copolymers are also suitable for use herein. For example, a tapered block copolymer is one in which the linkage between the A and B blocks is a copolymer which is richer in A units but gradually becomes richer in B units.

The block copolymer may be used in the elastomeric composition in an amount effective to achieve the desired mechanical properties, such as tensile, elastic and stress relaxation properties. The block copolymer will generally be present in the elastomeric composition in an amount typically from about 1 to about 99 weight percent, preferably from about 20 to about 80 weight percent, and more preferably from about 30 to about 70 weight percent, of the composition.

Various thermoplastic polymers or blends may be used in the elastomeric compositions of various embodiments of the present invention. Suitable thermoplastic polymers should preferably associate with the hard blocks of the block copolymers to form an entangled three-dimensional network. Not intending to be bound by theory, this entangled network structure is believed to be capable of improving the tensile, elastic and stress relaxation properties. Thermoplastic polymers such as polyphenylene oxide, and vinylarene resins derived from monomers including styrene, a-methyl styrene, other styrene derivatives, vinyl toluene, and mixtures thereof, are useful in the present invention. These polymers are generally considered to be chemically compatible with the styrenic hard blocks of the block copolymer. It is believed to be advantageous for the components to be compatible such that they may more easily form an entangled three-dimensional network structure, and they do not physically separate to a significant extent from the network structure.

Additional exemplary temperature-responsive materials include polyolefins (i.e., polypropylene, polyethylene, etc.) having an induced crystallization or orientation. For example, to induce an orientation in a polyolefin, the polyolefin may be strained and held at a set temperature above ambient temperature to reorient molecules within the structure, then returned to ambient temperature. Upon exposure to a temperature above ambient temperature, the molecular orientation varies and stiffness can be changed.

It should be appreciated that as the material is bent (e.g., while the fastener 40 is being connected), the resulting heat can cause a reduction of stiffness that reduces the ability of the tab member 40 to press into the wearer's skin. Furthermore, the wearer's own body heat can be sufficient to cause the reduction in stiffness. Advantageously, the stiffness can increase once the thermal increase abates and the variable stiffness member 80 returns to room temperature (e.g., when the article 20 is removed from the wearer). Alternatively, a heat source could be disposed adjacent the fastening device 41 and integral with the article 20 as disclosed in U.S. Pat. No. 6,791,004 issued to Cornelia Sprengard-Eichel, et al., on Sep. 14, 2004 such that an internal stimulus in the form of temperature fluctuations causes the heat-responsive tab member 42 to undergo a stiffness reduction.

Alternatively still, the variable stiffness member 80 comprises a material or combination of materials, such as ethylene vinyl alcohol copolymer (EVOH) that is responsive to moisture, either in vapor or liquid form, (e.g., humidity fluctuations). Specifically, as the humidity of the environment surrounding the EVOH variable stiffness member 80 increases (or as the liquid content of the EVOH variable stiffness member 80 increases), the stiffness of the variable stiffness member 80 and thus the tab member 42 correspondingly decreases. Moreover, a humidity source can be integral with the absorbent article, as described above with reference to the bladder 81 (see FIGS. 17A-B), thus providing an internal stimulus to the humidity-responsive variable stiffness member 80.

In accordance with yet another embodiment, the variable stiffness member 80 can be constructed of a brittle material, or combination of materials that have a relatively high modulus but low elongation capacity. Suitable examples include glass, ceramic, cement, concrete, stone, wood, or the like, that will fracture at a plurality of locations substantially simultaneously (i.e., shatter) in response to a predetermined force, which need not be a bending force, but could instead be a linear force (i.e., impact) in any suitable direction alone or in combination with a bending force that will produce the desired stiffness reduction. Such materials may further be thermoplastic (e.g., polystyrene, ABS, and polyvinyl chloride) or thermoset (e.g., epoxy resins, vinyl ester resins (such as pisphenol A), and polyimides).

In one aspect of the invention, the brittle material has a low or no ductility, such as sandstone, having an ultimate tensile strength of about 7 MPa, a compressive strength of about 85 MPa, a shear strength of about 14 MPa, a modulus of elasticity of about 40 GPa, and a modulus of rigidity of about 2 GPa. A suitable brittle material can have an elongation less than 5% before catastrophic failure. The term "catastrophic failure" is used herein to refer to a substantial change in bending resistance of the type that occurs when a brittle material fails at multiple locations. The variable stiffness member 80 is disposed above the tab element 43 and below the second substrate layer 71 as illustrated. Failure of the variable stiffness member 80 can thus be caused by a sufficient force applied to the variable stiffness member 80 during connection of fastening system 40 or by normal movement of the wearer during use. In this embodiment, it may be desirable to encase the variable stiffness member 80 as illustrated in FIG. 20 in order to prevent any loose or broken fragments from contacting the wearer's skin upon failure of the variable stiffness member 80.

Alternatively still, the variable stiffness member 80 is formed from a material that is intermixed in the surrounding stiffness element materials of one or more fastening elements. In this embodiment, the variable stiffness member 80 provides initial stiffness enhancement of the fastening element(s) until the predetermined stimulus causes deformation of the variable stiffness member 80. The force and/or resulting deformation, in turn, reduces the stiffness of the additive material-containing element. Such materials can be highly malleable and/or ductile, such as clay, memory foam, styrofoam, and lead.

One skilled in the art will appreciate that each of the above-described embodiments of the variable stiffness member 80 could be used alone or in combination with any of the fastening system components, either alone or in combination. For instance, the variable stiffness member 80 can be associated with any component(s) of tab member 42 and/or slot member 44 as described above such that the overall stiffness is reduced in response to the predetermined external stimulus. In particular, the variable stiffness member 80 can alternatively be associated with the tab substrate carrier 51, the first substrate layer 55, the core member 53, the second substrate layer 71, the slot element base member 76, the slot reinforcing member(s) 78, or any other component of a slot or tab member that would impact the overall stiffness of the corresponding member to which the variable stiffness member 80 is associated, either alone or in any combination.

It should be further appreciated that the principles of the present invention are not intended to be limited to tab-and-slot fasteners. Rather, one having ordinary skill in the art will appreciate that any desired element on an absorbent article can include a variable stiffness member of the type described above. For instance, a variable stiffness member of the type described above could be integrated into any other type of fastener found in an absorbent article. Nonlimiting examples of fasteners that could benefit from teachings of the present invention include hook and loop type fasteners, tape/DFS, cohesives, selective adhesives, a hermaphrodidic fastener, magnets, buttons, buckles, and the like. The variable stiffness member 80 could be integral with the fastener and/or operatively associated with it, as described above. For instance, in the context of a hook and loop type fastener, the variable stiffness member 80 could be integral with one or more hooks and/or loops (or their corresponding carrier members), and/or a separate element that is added to the hook and/or loop carrier member.

In accordance with certain aspects of the present invention, one method used to test for a desired level of stiffness reduction after a given deformation cycle uses a testing apparatus that can be any suitable tensile and compressive testing apparatus capable of holding a sample, setting the appropriate gage length, compressing the sample to be tested at a controlled rate, and measuring the resulting load of the part onto the testing apparatus without any interference or inaccuracy caused by the testing apparatus. An example of a suitable testing apparatus is a Synergie 200 Tensile Tester model number SYN200 equipped with a computer interface having TestWorks™ for Windows™ version 3.10 or later, both of which are commercially available from MTS® located in Minneapolis, Minn.

The testing apparatus is outfitted with a suitable load cell within 10% and 90% of the load range used during testing (e.g., a 10 Newton load cell or a 100 Newton load cell depending on the stiffness levels that are being tested). The testing apparatus includes flat grip faces capable of holding the fastener elements without slippage during the test. The testing apparatus should be located in a temperature and humidity controlled environment, or should be capable of holding the fastener elements in a controlled environment. Accordingly, a stiffness reducing stimulus of temperature and/or humidity can be applied to the fastener element as desired.

When subjecting a given fastener element to a compression test, the fastener element samples should equilibrate and be maintained at 23° C. and 50%±2% humidity for at least two hours before testing, unless otherwise indicated. Next, the first fastener element is clamped into the top grips on the MTS® Synergie 200 testing apparatus, or in the grips that are attached to the load cell input. The fastener element should be gripped at one end such that 20% of the length of the fastener element is held by the grip face, thus resulting in the fastener element being centered after the second grip is engaged with the gage length set to approximately 60% of the fastener element length. If the variable stiffness member 80 is not centrally disposed in the fastener element, the position of the grips should be adjusted such that the stiffness member 80 is centered in the grips (unless the member 80 spans the entire distance between the grips, in which case the stiffness member 80 would not need to be centered between the grips). At least 5 mm of the fastener element should be held by the grips once the second grip is engaged. This configuration will cause the testing apparatus to apply a compressive force to the fastener element that causes the element to bend about the axis 122 (or about one or more axes extending parallel to axis 122) illustrated in FIG. 9, thus simulating the bending force applied to the fastener element during use. In the event that the fastener element is configured to exhibit stiffness reduction about any axis other than axis 122, the fastener element should be appropriately oriented such that the compression test causes the fastener element to bend about one or more axes extending substantially parallel to the desired axis.

Next, the load cell is set to a force of zero (±1 gram or 0.01 N). The fastener element is then clamped with the second set of grips. The force reading on the load cell should be less than ±10 grams or 0.10 N. If the reading is more than this, the fastener element should be discarded because the force applied to the fastener element during gripping may have already damaged the fastener element or caused the reduction in stiffness to occur prematurely. Once the fastener element is in place, the fastener element is compressed at a rate of 5 inches/minute until the fastener element length (defines as the distance from one fastener element edge to an opposing fastener element edge along an axis extending centrally between the opposing grips) is reduced by 23%. As the fastener element is being compressed, the testing apparatus should be outputting the force applied to the sample throughout the deformation cycle. The peak force measured after during the compression is used to determine the stiffness reduction of the fastener element, as will now be described.

Figure 21A:
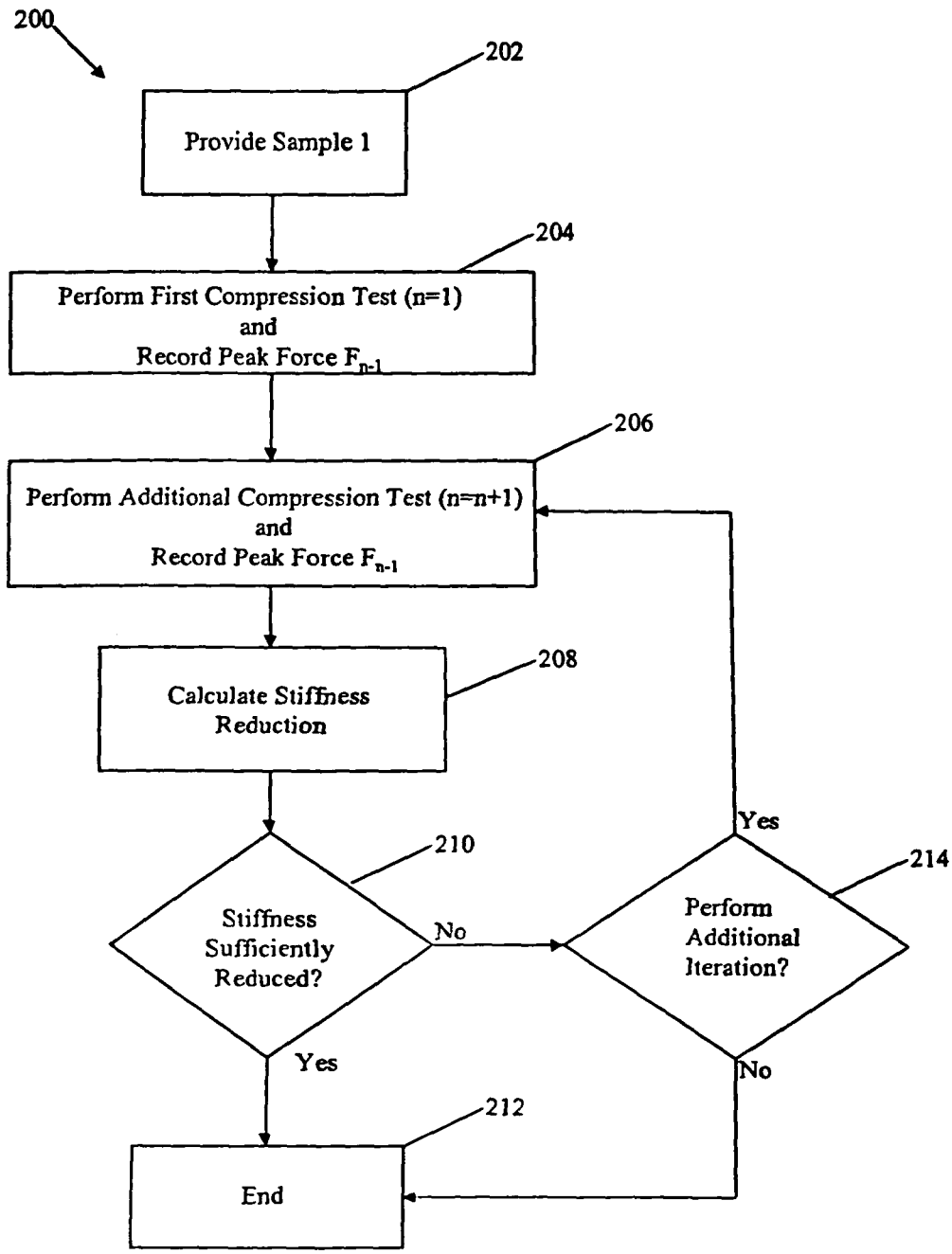
FIG. 21A is a flow chart illustrating a method for testing for sufficient stiffness reduction in accordance with one aspect of the invention.

Specifically, referring to FIG. 21A, a method 200 is provided to test for a force-responsive stiffness reduction upon completion of a given number of deformation cycles. Method 200 begins at step 202 whereby a fastener element to be tested is provided. The fastener element can include any of the variable stiffness members 80 described above. Next, at step 204, the fastener element is subjected to a first compression test of the type described above, and the peak force during compression is recorded. Because the peak force is reflective of the status of the fastener element prior to the instant compression test, the peak force can be expressed as $F_{n-1}$ or, in this case, $F_0$. The peak force is an indication of the original stiffness of the fastener element prior to any deformation of the fastener element.

Next, the fastener element is subjected to a subsequent compression test at step 206. Again, the peak force during compression is recorded. It should be appreciated that the peak force measured at step 206 is a reflection of the first deformation cycle of step 204. Once the subsequent compression test has been completed, the number of deformation cycles equals "2". However, because the peak force measured at step 206 is reflective of the previous compression cycle performed at step 204, the peak force is expressed as $F_{n-1}$ or, in this case, $F_1$. Once both peak forces have been measured, the percentage stiffness reduction resulting from a first deformation cycle can be calculated at step 208 as follows: $[(F_0-F_1)/F_0]*100\%$. If the percentage stiffness has been reduced as described above (e.g., stiffness reduction by a percentage of the original stiffness that is within a range defined at its lower end by and between 10%, 20%, 30%, 40%, and 50%, and defined at its upper end by and between 80%, 90%, 99%, and up to 100%), then the fastener element will be deemed, at decision block 210, to have undergone a suitable stiffness reduction for the purposes of reducing wearer discomfort and/or skin marking and/or irritation during use compared to fasteners that do not undergo the suitable stiffness reduction. The method 200 then ends at step 212.

If, on the other hand, the stiffness has not been sufficiently reduced as determined at decision block 210, method 200 advances to decision block 214 where it is determined whether additional deformation cycles are to be applied to the fastener element being tested. For instance, if it is desired only to determine whether the fastener element has achieved the desired stiffness reduction after one deformation cycle, the process can end at 212. Alternatively, if it is desired to test the fastener element for stiffness reduction after a greater number of deformation cycles, the method can revert to step 206, whereby an additional compression test is performed on the fastener element. The number of deformation cycles is then set to "3" and the peak force $F_2$ is recorded and compared to the peak force F0 to determine the stiffness reduction after two deformation cycles at step 208.

The process is repeated until the stiffness reduction of the fastener element has been tested for stiffness reduction after a desired number of deformation cycles. It should be appreciated that if a fastener element is being tested for stiffness reduction after a number of deformation cycles greater than one, steps 208 and 210 can be skipped until the desired number of deformation cycles has been applied to the fastener element.

Figure 21B:
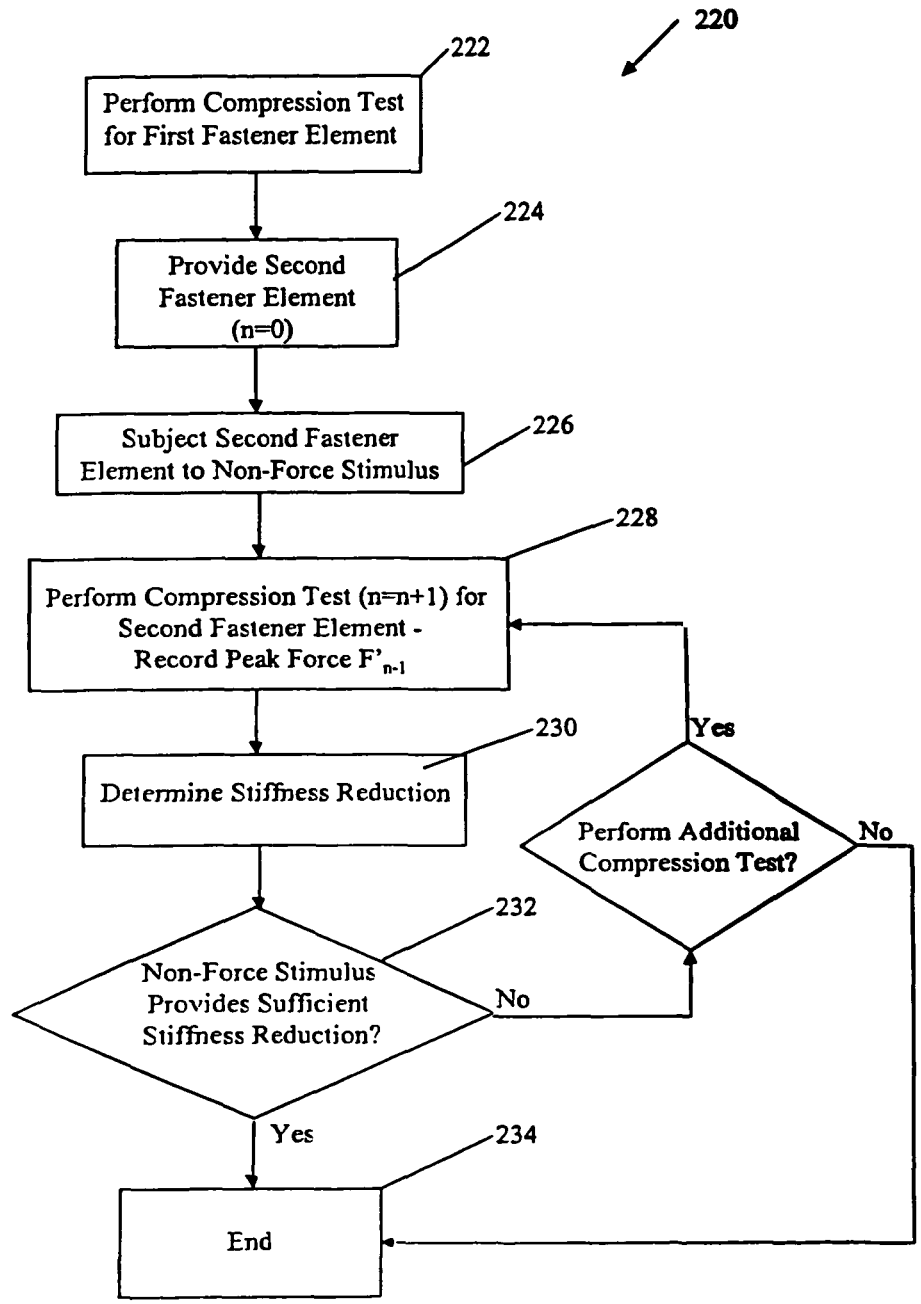
FIG. 21B is a flow chart illustrating a method for testing for sufficient stiffness reduction in accordance with another aspect of the invention.

Referring now to FIG. 21B, the present invention recognizes a method 220 for testing for suitable stiffness reduction resulting from both a non-force stimulus along with a combination of a force stimulus and a non-force stimulus. Method 220 begins at step 222, where a first fastener element is provided that is to be compression tested one time using steps 202 and 204 of the method 200. The peak force $F_0$ is then recorded to as a reflection of the initial stiffness of the first fastener element prior to any deformation.

At step 224, a second fastener element is provided, it being appreciated that the first and second fastener elements are selected from a group of normal production elements believed to be produced identically (or within normal manufacturing tolerances) such that the first and second fastener elements are substantially identical to each other. As a result, the behavior of the first element in response to a predetermined stimulus is substantially identical to the behavior of the second element in response to the stimulus. Because the second fastener element has not yet been compressed, the number of deformation cycles "n" is set to "0".

Next, at step 226, the second fastener element is subjected to a non-force stimulus of a type as described above (e.g., temperature, humidity, a change in internal pressure, or a combination thereof). The second fastener element should be allowed to equilibrate for a predetermined period of time (for instance fifteen minutes or greater, up to two hours) at the desired temperature and/or humidity settings before the method 220 proceeds to step 228. At step 228, a compression test is performed as described above, and the number of deformation cycles "n" is set to "1". The peak force applied during the compression test is also recorded for the second fastener element as $F'_0$, it being appreciated that the peak force is representative of the original stiffness of the second fastener element and the stiffness varying effects of the non-force stimulus.

Accordingly, at step 230, the stiffness reduction caused by the non-force stimulus can be determined by comparing the peak force of the first fastener element recorded at step 206 to the peak force of the second fastener element recorded at step 228. Specifically, the percentage stiffness reduction attributable to the non-force stimulus is calculated as $[(F_0-F'_0)/F_0]*100$. Next, at decision block 232, it is determined whether the calculated stiffness reduction of the fastener element is sufficient for the purposes of reducing discomfort and/or skin marking and/or irritation during use compared to a fastener element lacking the stiffness reduction characteristics. If so, the method 220 ends at step 234.

If the non-force stimulus alone was insufficient to produce the desired stiffness reduction, method proceeds to decision block 236 where it is determined whether to repeat the compression test. If not, the method 220 terminates at step 234. If an additional compression test is desired, the method 230 reverts to step 228 for the purposes of determining whether a combination of force stimulus and non-force stimulus is sufficient to provide the desired stiffness reduction. At step 228, the second fastener element is again subjected to a compression test to determine the stiffness of the second fastener element resulting from both the non-force stimulus and the first compression test. The number of deformation cycles "n" is set to "2", and the peak force $F'_1$, is recorded. Next, at step 230, the percentage stiffness reduction attributable to the non-force stimulus and one deformation cycle (i.e., force stimulus) is calculated as $[(F_0-F'_1)/F_0]*100$. If the force reduction is sufficient as determined at decision block 232, it is determined that the fastener element achieved the desired stiffness reduction after being subjected to one deformation cycle and the non-force stimulus.

If it is determined that the fastener element has not achieved the desired stiffness reduction, the method 220 can revert to step 228 to complete additional deformation cycles as desired.

As described above, the topsheet 22 is generally a portion of the diaper 20 that can be positioned at least in partial contact or close proximity to a wearer. Accordingly, the topsheet 22 can be supple, soft feeling, and non-irritating to a wearer's skin. Generally, at least a portion of the topsheet 22 is liquid pervious, permitting liquids (e.g., urine) to readily penetrate through its thickness. The topsheet 22 can be made of a hydrophobic material to isolate the wearer's skin from liquids contained in the absorbent core 26. Suitable topsheets 22 can be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. A suitable topsheet 22 is available from BBA Fiberweb, Brentwood, Tenn. as supplier code 055SLPV09U. Other examples of suitable topsheets 22 are described in U.S. Pat. No. 3,929,135, issued to Thompson on Dec. 30, 1975; U.S. Pat. No. 4,324,246 issued to Mullane et al. on Apr. 13, 1982; U.S. Pat. No. 4,342,314 issued to Radel et al on Aug. 3, 1982; U.S. Pat. No. 4,463,045 issued to Ahr et al. on Jul. 31, 1984; and U.S. Pat. No. 5,006,394 issued to Baird on Apr. 9, 1991.

Any portion of the topsheet 22 can be coated with a lotion as is known in the art. Examples of suitable lotions include those described in U.S. Pat. Nos. 5,607,760; 5,609,587; 5,635,191; and 5,643,588. The topsheet 22 can be fully or partially elasticized or can be foreshortened so as to provide a void space between the topsheet 22 and the core 26. Exemplary structures including elasticized or foreshortened topsheets are described in more detail in U.S. Pat. Nos. 4,892,536; 4,990,147; 5,037,416; and 5,269,775.

The absorbent core 26 generally is disposed between the topsheet 22 and the backsheet 24. The absorbent core 26 typically comprises a storage layer, which can be partially or totally surrounded by a core wrap. The storage layer can comprise any absorbent material that is generally compressible, conformable, non-irritating to the wearer's skin, and capable of absorbing and retaining liquids such as urine and other certain body exudates. The storage layer can comprise a wide variety of liquid-absorbent materials commonly used in disposable diapers and other absorbent articles such as comminuted wood pulp, which is generally referred to as air felt or fluff. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers (such as superabsorbent fibers), absorbent gelling materials, or any other known absorbent material or combinations of materials. Examples of some combinations of suitable absorbent materials are fluff with absorbent gelling materials and/or superabsorbent polymers, and absorbent gelling materials and superabsorbent fibers etc. In one optional embodiment the storage layer is air felt free, that is, it contains no air felt. The storage layer can further comprise minor amounts (typically less than 10%) of non-liquid absorbent materials, such as adhesives, waxes, oils and the like.

Exemplary absorbent structures for use as the absorbent assemblies are described in U.S. Pat. No. 4,834,735, entitled "High Density Absorbent Members Having Lower Density and Lower Basis Weight Acquisition Zones", issued to Alemany et al. on May 30, 1989; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997.

In one optional embodiment of the present invention the absorbent core comprises, in addition to the storage layer and the durable hydrophilic core wrap, an acquisition system, which comprises an upper acquisition layer facing towards the wearer and a lower acquisition layer. In one embodiment the upper acquisition layer comprises a nonwoven fabric whereas the lower acquisition layer comprises a mixture of chemically stiffened, twisted and curled fibers, high surface area fibers and thermoplastic binding fibers. In another embodiment both acquisition layers are provided from a nonwoven material, which can be hydrophilic. The acquisition layer is in direct contact with the storage layer. Furthermore, the storage layer or parts thereof, such as the upper acquisition layer, can optionally be coated with the hydrophilicity boosting composition.

The backsheet 24 can be impervious to liquids (e.g., urine) and manufactured from a thin plastic film or a nonwoven web, although other flexible liquid impervious materials which are compliant and will readily conform to the general shape and contours of the human body can also be used. The backsheet 24 is generally positioned such that it can be at least a portion of the garment-facing surface of the diaper 20. Backsheet 24 prevents the exudates absorbed and contained therein from soiling articles that can contact the diaper 20, such as bed sheets and undergarments. Suitable backsheet 24 materials include films such as those manufactured by Tredegar Industries Inc. of Terre Haute, Ind. and sold under the trade names X15306, X10962, and X10964. The backsheet can be a thermoplastic film having a thickness of from about 0.012 mm (0.5 mil) to about 0.051 mm (2.0 mils).

Other suitable backsheet 24 materials can include breathable materials that permit vapors to escape from the diaper 20 while still preventing exudates from passing through the backsheet 24. Exemplary breathable materials can include materials such as woven webs, nonwoven webs, polymeric films such as thermoplastic films of polyethylene or polypropylene, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537.

In one embodiment, the backsheet 26 can comprise a structural elastic-like film (SELF) web. SELF webs suitable for the present invention are more completely described in the commonly assigned U.S. Pat. No. 5,518,801 entitled "Web Materials Exhibiting Elastic-Like Behavior" issued to Chappell et al. on May 21, 1996.

Other suitable materials and/or manufacturing techniques can be used to provide a suitable backsheet 24 including, but not limited to, surface treatments, particular film selections and processing, particular filament selections and processing, etc. The backsheet 24 can be embossed and/or matte finished to provide a more clothlike appearance.

Backsheet 24 can also include more than one layer, as illustrated in the cut-away of FIG. 1. The backsheet 24 can comprise an outer cover 26a and an inner layer 26b. The outer cover 26a can have longitudinal edges 27a and the inner layer 26b can have longitudinal edges 27b. The outer cover 26a can be made of a soft, non-woven material. The inner layer 26b can be made of a substantially water-impermeable film. The outer cover 26a and an inner layer 26b can be attached together by adhesive or any other suitable material or method. A particularly suitable outer cover 26a is available from Corovin GmbH, Peine, Germany as supplier code A18AH0, and a particularly suitable inner layer 26b is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

FIG. 1 shows an embodiment of the diaper 20 in which the topsheet 22 and the backsheet 24 have length and width dimensions generally larger than those of the absorbent core 26. The topsheet 22 and the backsheet 24 extend beyond the edges of the absorbent core 26 to thereby form the periphery of the diaper 20. While the topsheet 22, the backsheet 24, and the absorbent core 26 can include many different materials and can be assembled in a variety of well known configurations, suitable diaper materials and configurations are described generally in U.S. Pat. No. 3,860,003 entitled "Contractable Side Portions for Disposable Diaper" which issued to Kenneth B. Buell on Jan. 14, 1975; and U.S. Pat. No. 5,151,092 issued to Buell on Sep. 9, 1992; and U.S. Pat. No. 5,221,274 issued to Buell on Jun. 22, 1993.

The diaper 20 can further include a pair of opposing and longitudinally extending leg cuffs 32 to improve containment of liquids and other body exudates. Each elasticized leg cuff 32 can include several different embodiments for reducing the leakage of body exudates in the leg regions. U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (leg cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a leg cuff 32.

The diaper 20 can also include a waist feature 30 that helps provide improved fit and containment. The waist feature 30 is that portion or zone of the diaper 20 which is intended to elastically expand and contract to dynamically fit the wearer's waist. The elastic waist feature 30 generally extends longitudinally outwardly from at least one of the waist edges 39 of the absorbent core 26 and generally forms at least a portion of the end edge 56 of the diaper 20. Although disposable diapers are generally constructed so as to have two elastic waist features, one positioned in the front waist region 36 and one positioned in the back waist region 36, diapers can be constructed with a single elastic waist feature 30. Further, while the elastic waist feature 30 or any of its constituent elements can include a separate element affixed to the diaper 20, the elastic waist feature 30 can be constructed as an extension of other elements of the diaper 20 such as the backsheet 24, the topsheet 22 or both the backsheet 24 and the topsheet 22. Examples of suitable waist features include those described in U.S. Pat. No. 4,515,595 issued to Kievit et al. on May 7, 1985 and the above referenced U.S. Pat. No. 5,151,092 issued to Buell on Sep. 9, 1992; and U.S. Pat. No. 5,221,274 issued to Buell on Jun. 22, 1993.

All documents cited in the Detailed Description of the Invention are, in relevant part, incorporated herein by reference, however the citation of any document is not construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It should be apparent that combinations of such embodiments and features are possible and can result in executions within the scope of this invention. It is therefore intended to cover in the appended claims all such changes and modifications that are within the scope of this invention.

What is claimed is:

1. An absorbent article having a front waist region, a back waist region opposed to the front waist region and a crotch region located between the front waist region and the back waist region, a pair of longitudinal edges and a pair of end edges, the absorbent article comprising:
   a topsheet;
   a backsheet attached to the topsheet; and
   a fastening system including at least one fastening device configured to connect a first article location to a second article location, the fastening device including a variable stiffness member having an original stiffness before experiencing a predetermined stimulus and a permanently reduced stiffness after experiencing the predetermined stimulus, wherein the reduced stiffness is at least 10% less than the original stiffness.

2. The absorbent article as recited in claim 1, wherein the fastening system further comprises:
   a slot member disposed on the absorbent article at a first location, the slot member including a slot member body defining an elongated slot;
   a tab member disposed on the absorbent article at a second location opposed to the first location, the tab member defining an elongated tab element portion configured to pass through the slot such that the tab element portion overlaps the slot member body.

3. The absorbent article as recited in claim 2, wherein the variable stiffness member is integral with at least one of the fastening device members.

4. The absorbent article as recited in claim 3, wherein the variable stiffness member comprises an additive that is intermixed with the at least one of the fastening device members.

5. The absorbent article as recited in claim 2, wherein the variable stiffness member is attached to at least one of the fastening device members.

6. The absorbent article as recited in claim 2, wherein the variable stiffness member comprises a geometric configuration of at least a portion of one of the members.

7. The absorbent article as recited in claim 2, wherein the geometric configuration defines at least one stress concentration.

8. The absorbent article as recited in claim 7, wherein the stress concentration is configured to plastically deform in response to the stimulus.

9. The absorbent article as recited in claim 7, wherein the stress concentration is configured to fracture in response to the stimulus.

10. The absorbent article as recited in claim 1, wherein the original stiffness is reduced by at least 20% to achieve the reduced stiffness.

11. The absorbent article as recited in claim 1, wherein the predetermined stimulus comprises an applied force.

12. The absorbent article as recited in claim 11, wherein the variable stiffness member has a ductility less than 5% elongation and is configured to shatter in response to the applied force.

13. The absorbent article as recited in claim 11, wherein the applied force is within the range of 50 g and 500 g.

14. The absorbent article as recited in claim 11, wherein the stiffness is reduced after no more than 5 deformation cycles of the applied force.

15. The absorbent article as recited in claim 1, wherein the predetermined stimulus is selected from the group consisting of a fluctuation in temperature, a fluctuation in humidity, and a fluctuation in internal pressure.

16. The absorbent article as recited in claim 15, wherein the variable stiffness member comprises a material having a polyolefin having an induced orientation.

17. The absorbent article as recited in claim 16, wherein the variable stiffness member comprises a material comprising a block copolymer having an order-disorder transition temperature within the range of about 86° and about 98.6° Fahrenheit.

18. The absorbent article as recited in claim 1, further comprising an absorbent core disposed between the topsheet and the backsheet.

19. A fastening device for fastening a first member to a second member, the fastening device comprising:
   a first fastener element extending from the first member;
   a second fastener element extending from the second member at a location opposed to the first member, the second fastener element configured to engage the first fastener element; and
   a variable stiffness member having an original stiffness before experiencing a predetermined stimulus and a permanently reduced stiffness after experiencing the predetermined stimulus, wherein the reduced stiffness is at least 10% less than the original stiffness.

20. The fastening device as recited in claim 19, wherein the predetermined stimulus is selected from the group consisting of an applied force, a temperature fluctuation, a humidity fluctuation, and a fluctuation of internal pressure.

21. The fastening device as recited in claim 20, wherein the applied force is between 50 g and 500 g.

22. The fastening device as recited in claim 21, wherein the original stiffness is reduced by at least 10% to achieve the reduced stiffness.

23. A method for releasable fastening an absorbent article onto the body of a wearer, the article being of the type having a front waist region, a back waist region opposed to the front waist region, and a crotch region located between the front waist region and the back waist region, a fastening device comprising a tab member configured to releasably connect to a slot member to fasten the article onto the body of the wearer, the fastening device including a variable stiffness member having an original stiffness before experiencing a predetermined stimulus and a permanently reduced stiffness after experiencing the predetermined stimulus, wherein the reduced stiffness is less than the original stiffness, the method comprising the steps of:
   (A) connecting the tab and slot members;
   (B) applying the predetermined stimulus to the variable stiffness member; and
   (C) reducing a stiffness of the fastening device at least 10% from the original stiffness to the reduced stiffness.

* * * * *